(12) United States Patent
Hara et al.

(10) Patent No.: US 9,370,589 B2
(45) Date of Patent: Jun. 21, 2016

(54) SWITCHING FLUORESCENT NANOPARTICLE PROBE AND FLUORESCENT PARTICLE IMAGING METHOD USING SAME

(75) Inventors: Isao Hara, Kyoto (JP); Eiichi Ozeki, Kyoto (JP); Hideo Saji, Kyoto (JP); Shunsaku Kimura, Hirakata (JP); Masahiro Ono, Uji (JP); Takashi Temma, Kyoto (JP)

(73) Assignees: SHIMADZU CORPORATION, Kyoto (JP); KYOTO UNIVERSITY, Kyoto (JP)

(*) Notice: Subject to any disclaimer, the term of this patent is extended or adjusted under 35 U.S.C. 154(b) by 102 days.

(21) Appl. No.: 13/818,392
(22) PCT Filed: Aug. 8, 2011
(86) PCT No.: PCT/JP2011/068071
§ 371 (c)(1),
(2), (4) Date: Feb. 22, 2013
(87) PCT Pub. No.: WO2012/026316
PCT Pub. Date: Mar. 1, 2012

(65) Prior Publication Data
US 2013/0149252 A1 Jun. 13, 2013

(30) Foreign Application Priority Data
Aug. 23, 2010 (JP) .................................. 2010-186701

(51) Int. Cl.
*A61K 9/14* (2006.01)
*A61K 49/00* (2006.01)

(52) U.S. Cl.
CPC .......... *A61K 49/0089* (2013.01); *A61K 49/0032* (2013.01); *A61K 49/0093* (2013.01); *Y10S 977/773* (2013.01); *Y10S 977/927* (2013.01)

(58) Field of Classification Search
None
See application file for complete search history.

(56) References Cited

U.S. PATENT DOCUMENTS 5,723,591 A * 3/1998 Livak et al. .................. 536/22.1
6,083,486 A 7/2000 Weissleder et al.
(Continued)

FOREIGN PATENT DOCUMENTS

JP 2002-514610 5/2002
JP 2005-220045 A 8/2005
(Continued)

OTHER PUBLICATIONS

A Makino, R Yamahara, E Ozeki, S Kimura. "Preparation of Novel Polymer Assemblies, "Lactosome", Composed of Poly(L-lactic acid) and Poly(sarcosine)." Chemistry Letters, vol. 36 No. 10, 2007, pp. 1220-1221.*

(Continued)

*Primary Examiner* — Isaac Shomer
(74) *Attorney, Agent, or Firm* — Cheng Law Group, PLLC

(57) ABSTRACT

The present invention provides a novel fluorescent nanoparticle imaging probe having a switching function (a function to quench a fluorescent dye during nanoparticle preparation, and emit fluorescence during imaging). A switching fluorescent nanoparticle probe comprising: a molecular assembly composed of an amphiphilic block polymer having a hydrophilic block chain and a hydrophobic block chain; and a fluorescent dye encapsulated in the molecular assembly, wherein (a) the hydrophilic block chain comprises, as an essential hydrophilic structural unit, a unit selected from a sarcosine unit and an alkylene oxide unit, (b) the hydrophobic block chain comprises, as an essential hydrophobic structural unit, a unit selected from the group consisting of an amino acid unit and a hydroxylic acid unit, and (c) the fluorescent dye is a cyanine compound represented by the formula (I):

[Chemical formula 1]

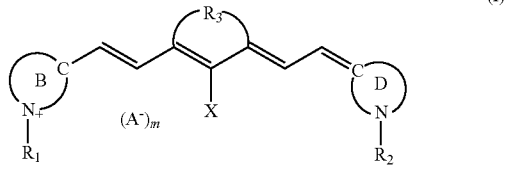

and two or more molecules of the fluorescent dye are encapsulated in the single molecular assembly.

16 Claims, 11 Drawing Sheets

(56) References Cited

U.S. PATENT DOCUMENTS

| | | | |
|---|---|---|---|
| 2008/0019908 A1 | 1/2008 | Akitsu et al. | |
| 2008/0274173 A1* | 11/2008 | Sill et al. | 424/450 |
| 2010/0068285 A1* | 3/2010 | Zale et al. | 424/489 |
| 2011/0104056 A1* | 5/2011 | Hara | A61K 9/5153 424/1.65 |

FOREIGN PATENT DOCUMENTS

| | | | |
|---|---|---|---|
| JP | 2008-24816 A | 2/2008 | |
| WO | WO-2009/012109 A2 | 1/2009 | |
| WO | WO 2009012109 A2 * | 1/2009 | |
| WO | WO-2009/148121 A1 | 12/2009 | |
| WO | WO 2009148121 A1 * | 12/2009 | A61K 9/5153 |
| WO | WO 2010/013137 A1 | 2/2010 | |

OTHER PUBLICATIONS

E Ozeki, R Yamahara, I Hara, E Tekeuchi. "Development of Molecular Probe with Using Nanocarder, "Lactosome", Composed of Amphiphilic Polydepsipeptide, Poly(Lqactic acid) and Poly(sarcosine)", Shimadzu Review, Sep. 2009, vol. 66, No. 1-2, pp. 3-12.*

International Search Report for the Application No. PCT/JP2011/068071 mailed Aug. 30, 2011.

Kidchob, Tongjit et al., "Amphiphilic poly(Ala)-*b*-poly(Sar) microspheres loaded with hydrophobic drug", Journal of Controlled Release, 1998, vol. 51, pp. 241-248.

Makino, Akira et al., "Preparation of Novel Polymer Assemblies, "Lactosome", Composed of Poly(L-lactic acid) and Poly(sarcosine)", Chemistry Letters, 2007, vol. 36, No. 10, pp. 1220-1221.

Mujumdar, Swati et al., "Cyanine-Labeling Reagents: Sulfobenzinclocyanine Succinimidyl Esters", Bioconjugate Chem., 1996, vol. 7, No. 3, pp. 356-362.

Yoichi, Shimizu et al., The Pharmaceutical Society of Japan, Mar. 29, 2010, 130 poster, 29P-am395Q, (Abstract).

Tung, Ching-Hsuan et al., "In Vivo Imaging of Proteolytic Enzyme Activity Using a Novel Molecular Reporter", Cancer Research, Sep. 1, 2000, vol. 60, pp. 4953-4958.

Lin, Yuhui et al., "Novel Near-Infrared Cyanine Fluorochromes: Synthesis, Properties, and Bioconjugation", Bioconjugate Chem., 2002, vol. 13, No. 3, pp. 605-610.

Ogawa, Mikako et al., "In vivo Molecular Imaging of Cancer with a Quenching Near-Infrared Fluorescent Probe Using Conjugated of Monoclonal Antibodies and Indocyanine Green", Cancer Research, Feb. 15, 2009, vol. 69, No. 4, pp. 1268-1272.

Yoichi, Shimizu et al., The Pharmaceutical Society of Japan, 130 poster, Mar. 5, 2010, 29P-am395Q, p. 118.

Flanagan, James et al., "Functionalized Tricarbocyanine Dyes as Near-Infrared Fluorescent Probes for Biomolecules", Bioconjugate Chem., 1997, vol. 8, No. 5, pp. 751-756.

Ozeki, Eiichi et al., "Development of Molecular Probe with Using Nanocarrier, "Lactosome", Composed of Amphiphilic Polydepsipeptide, Poly(L-lactic acid) and Poly(sarcosine)", Shimadzu Review, Sep. 2009, vol. 66, No. 1-2, pp. 3-12.

Yoichi, Shimizu et al., The Pharmaceutical Society of Japan, 129 poster, Mar. 5, 2009, 26N-pm16, p. 87.

Yoichi, Shimizu et al., The Pharmaceutical Society of Japan, 131 poster, Mar. 5, 2011, 30L-pm01, p. 101.

International Preliminary Report on Patentability for Application No. PCT/JP2011/068071 mailed Mar. 28, 2013.

Supplementary European Search Report for the Application No. EP 11 81 9780 dated Apr. 7, 2015, 6 printed pages.

Tanisaka, Hiroki et al., "Near-Infrared Fluorescent Labeled Peptosome for Application to Cancer Imaging", Bioconjugate Chemistry, 2008, vol. 19, No. 1, pp. 109-117.

Yang, Zhi et al., "Long-Circulating Near-Infrared Fluorescence Core-Crosslinked Polymeric Micelles: Synthesis, Characterization, and Dual Nuclear/Optical Imaging", Biomacromolecules, 2007, vol. 8, No. 11, pp. 3422-3426.

* cited by examiner

SWITCHING FLUORESCENT NANOPARTICLE PROBE AND FLUORESCENT PARTICLE IMAGING METHOD USING SAME

TECHNICAL FIELD

The present invention relates to a fluorescent nanoparticle comprising a molecular assembly composed of an amphiphilic substance having biocompatibility and a fluorescent dye encapsulated in the molecular assembly, and fluorescence imaging using the fluorescent nanoparticle as a probe.

BACKGROUND ART

In recent years, there has been increasing interest in nanotechnology, and novel functional materials utilizing properties unique to nanosized substances have been developed. Such novel functional materials can be applied to a wide variety of fields such as energy, electronics, and medical and pharmaceutical fields. Among them, nanotechnology has received attention for the detection of substances in biological samples and in vivo imaging.

In medical and pharmaceutical fields, attention has been given to a near-infrared fluorescence photography method for imaging a tumor site by accumulation of a near-infrared fluorescent dye in the tumor site. In this method, a compound having the property of emitting fluorescence in the near-infrared region by irradiation with excitation light is administered as an imaging agent to a living body. Then, the living body is externally irradiated with excitation light having a near-infrared wavelength, and fluorescence emitted from the fluorescent imaging agent accumulated in a tumor site is detected to determine a lesion site.

A substance used as an imaging probe is mainly composed of a carrier agent and a fluorescent dye, and various carrier agents and fluorescent dyes have been reported.

Examples of the carrier agent include a liposome nanoparticle (JP-A-2005-220045 (Patent Document 1)), a peptidic nanoparticle (Journal of Controlled Release 51 (1998) 241-248 (Non-Patent Document 1)), a nanoparticle using an amphiphilic block polymer having, as a hydrophobic block, poly glutamic acid methyl ester (JP-A-2008-024816 (Patent Document 2)), a nanoparticle using an amphiphilic block polymer composed of a polysarcosine chain and a polylactic acid chain (Chemistry Letters, vol. 36, no. 10, 2007, p. 1220-1221 (Non-Patent Document 2)), and a nanoparticle using an amphiphilic block polymer composed of a polysarcosine chain and a polylactic acid chain, and a polylactic acid (WO 2009/148121 (Patent Document 3)).

The fluorescent dye is covalently bound to or non-covalently encapsulated in the carrier agent, and a fluorescein-based dye, a cyanine-based dye, a rhodamine-based dye, or the like is used. As the cyanine-based dye, indocyanine green (ICG) is often used, but various indocyanine derivatives have been developed (Bioconjugate Chem. 1996, 7, 356-362 (Non-Patent Document 3), The 131st Annual Meeting of The Pharmaceutical Society of Japan, 29p-am395Q poster, Mar. 29, 2010 (Non-Patent Document 4)). Further, methods have been reported which allow nanoparticles quenched by encapsulation of both an indocyanine derivative and a quencher to acquire fluorescence when the nanoparticles reach a tumor tissue (Cancer Research, 60, 4953-4958, Sep. 1, 2000 (Non-Patent Document 5), Bioconjugate Chem. 2002, 13, 605-610 (Non-Patent Document 6), Cancer Research, 2009; 69: (4). Feb. 15, 2009 (Non-Patent Document 7)).

More specifically, Non-Patent Document 4 described above discloses the preparation of nanoparticles IC7-1 lactosome from 500 μL of a 6 mg/mL solution of an amphiphilic polymer composed of a polysarcosine chain and a polylactic acid chain (PSar$_{70}$-PLLA$_{30}$), and 3.16 μL of a 1 mg/mL solution of an indocyanine derivative IC7-1. That is, it has been disclosed that the amount of the indocyanine derivative IC7-1 encapsulated in the nanoparticle IC7-1 lactosome is 0.48 mol %. This amount of the encapsulated indocyanine derivative IC7-1 corresponds to 1 molecule per single nanoparticle IC7-1 lactosome.

PRIOR ART DOCUMENTS

Patent Documents

Patent Document 1: JP-A-2005-220045
Patent Document 2: JP-A-2008-024816
Patent Document 3: WO 2009/148121

Non-Patent Documents

Non-Patent Document 1: "Journal of Controlled Release", Vol. 51, 1998, pp. 241-248
Non-Patent Document 2: "Chemistry Letters", Vol. 36, No. 10, 2007, pp. 1220-1221
Non-Patent Document 3: "Bioconjugate Chemistry", 1996, Vol. 7, pp. 356-362
Non-Patent Document 4: The 131st Annual Meeting of The Pharmaceutical Society of Japan, 29p-am395Q poster, Mar. 29, 2010
Non-Patent Document 5: "Cancer Research", Vol. 60, pp. 4953-4958, Sep. 1, 2000
Non-Patent Document 6: "Bioconjugate Chemistry", 2002, Vol. 13, pp. 605-610
Non-Patent Document 7: "Cancer Research", 2009; Vol. 69: (No. 4), Feb. 15, 2009

SUMMARY OF THE INVENTION

Problems to be Solved by the Invention

It is an object of the present invention to provide a novel fluorescent nanoparticle imaging probe having a switching function (i.e., a function to quench an encapsulated fluorescent dye during nanoparticle preparation, and emit fluorescence during imaging).

Means for Solving the Problems

The present inventors have intensively studied, and as a result, have found that a self-quenching nanoparticle by encapsulating a high concentration of fluorescent dye has the extraordinary effect of recovering fluorescence by contact with a blood component. This finding has led to the completion of the present invention.

The present invention includes the following switching fluorescent nanoparticle probe and imaging method using the same.

(1) A fluorescent nanoparticle probe comprising:
  a molecular assembly composed of an amphiphilic block polymer having a hydrophilic block chain and a hydrophobic block chain; and
  a fluorescent dye encapsulated in the molecular assembly,
wherein
  (a) the hydrophilic block chain comprises, as an essential hydrophilic structural unit, a unit selected from a sarcosine unit and an alkylene oxide unit, and has the 20 or more essential hydrophilic structural units, (b) the hydrophobic block chain comprises, as an essential hydrophobic structural unit, a unit selected from the group consisting of an amino acid unit and a hydroxylic acid unit, and has the 15 or more essential hydrophobic structural units, and (c) the fluorescent dye is a cyanine compound represented by the following structural formula (I)

[Chemical formula 1]

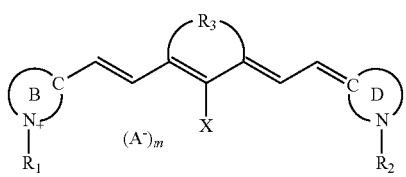

(I)

wherein $R_1$ and $R_2$ may be the same or different from each other and each is a hydrocarbon group which may be substituted; $R_3$ is a bivalent hydrocarbon group which may be substituted; X is a halogen, an aryloxy group, or a thioaryloxy group; $A^-$ is an anion and m is 0 or 1; and a ring B and a ring D may be the same or different from each other and each is a nitrogen-containing bicyclic or tricyclic aromatic heterocycle, and two or more molecules of the fluorescent dye are encapsulated in the single molecular assembly.

In the above-described switching fluorescent nanoparticle probe, fluorescence is quenched by the association of two or more molecules of the encapsulated fluorescent dye.

(2) The fluorescent nanoparticle probe according to (1), wherein the fluorescent dye is encapsulated in the molecular assembly in an amount of 1 to 50 mol % with respect to a total amount of the amphiphilic block polymer and the fluorescent dye.

The above-described amount of the fluorescent dye encapsulated in the fluorescent nanoparticle corresponds to 2 to 200 molecules of the fluorescent dye per particle.

(3) The fluorescent nanoparticle probe according to (1) or (2), wherein fluorescence intensity in plasma is 10 times or more higher than that in phosphate buffered saline.

One example of the case where the fluorescence intensity is 10 times is a case where the amount of the encapsulated fluorescent dye is 20 mol % (i.e., corresponding to 50 molecules of the fluorescent dye per fluorescent nanoparticle).

(4) The fluorescent nanoparticle probe according to any one of (1) to (3), wherein the ring B has either of the following structures:

[Chemical formula 2]

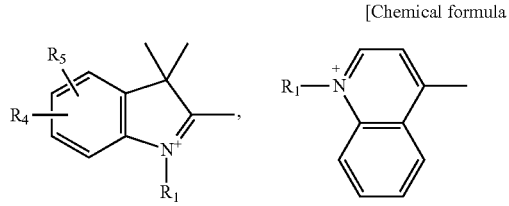

wherein $R_4$ and $R_5$ are hydrogen or are linked together to form an aryl ring; and the ring D has either of the following structures:

[Chemical formula 3]

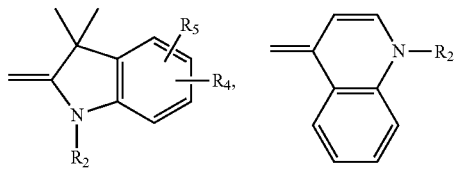

wherein $R_4$ and $R_5$ are hydrogen or are linked together to form an aryl ring.

(5) The fluorescent nanoparticle probe according to any one of (1) to (4), wherein the cyanine compound is an indocyanine compound represented by the following structural formula (I-i):

[Chemical formula 4]

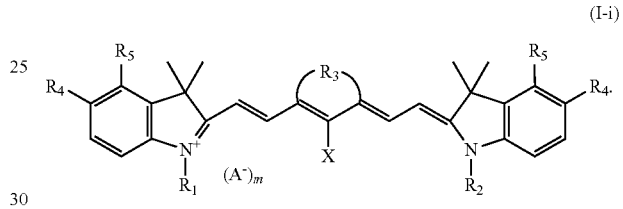

(I-i)

(6) The fluorescent nanoparticle probe according to any one of (1) to (5), wherein the fluorescent dye is represented by the following structural formula (I-ii):

[Chemical formula 5]

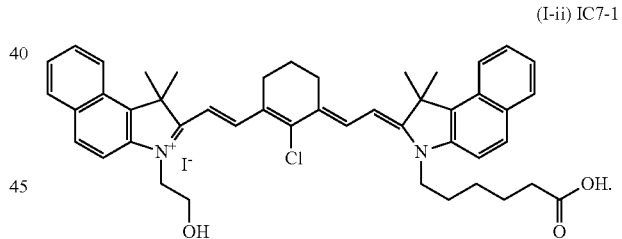

(I-ii) IC7-1

(7) The fluorescent nanoparticle probe according to any one of (1) to (5), wherein the fluorescent dye is represented by the following structural formula (I-iii):

[Chemical formula 6]

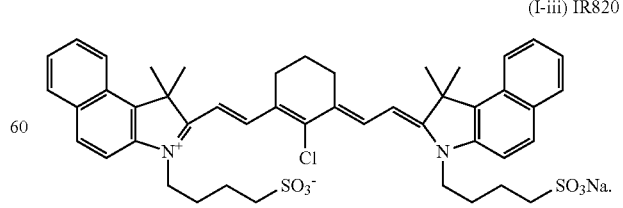

(I-iii) IR820

(8) The fluorescent nanoparticle probe according to any one of (1) to (5), wherein the fluorescent dye is represented by the following structural formula (I-iv):

[Chemical formula 7]

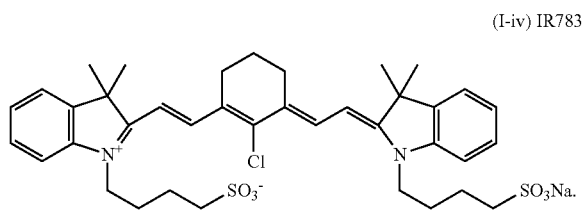

(I-iv) IR783

(9) The fluorescent nanoparticle probe according to any one of (1) to (5), wherein the fluorescent dye is represented by the following structural formula (I-v):

[Chemical formula 8]

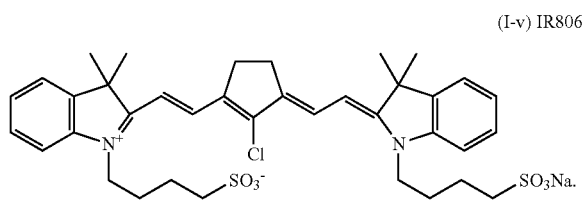

(I-v) IR806

(10) The fluorescent nanoparticle probe according to any one of (1) to (4), wherein the fluorescent dye is represented by the following structural formula (I-vi):

[Chemical formula 9]

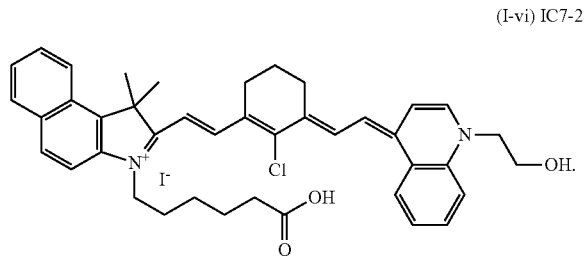

(I-vi) IC7-2

The fluorescent nanoparticle probe according to any one of (1) to (4), wherein the fluorescent dye is represented by the following structural formula (I-vii):

[Chemical formula 10]

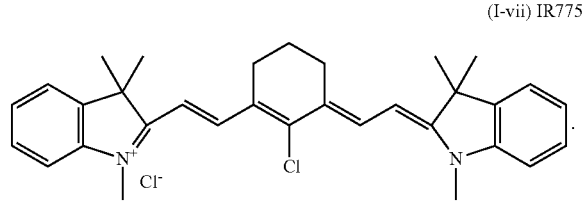

(I-vii) IR775

(12) The fluorescent nanoparticle probe according to any one of (1) to (4), wherein the fluorescent dye is represented by the following structural formula (I-viii):

[Chemical formula 11]

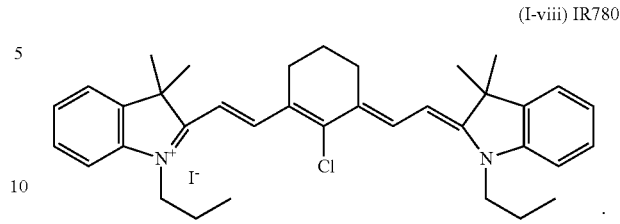

(I-viii) IR780

(13) The fluorescent nanoparticle probe according to any one of (1) to (4), wherein the fluorescent dye is represented by the following structural formula (I-ix):

[Chemical formula 12]

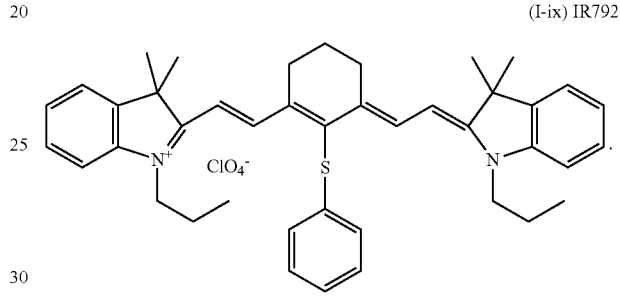

(I-ix) IR792

(14) The fluorescent nanoparticle probe according to any one of (1) to (4), wherein the fluorescent dye is represented by the following structural formula (I-x):

[Chemical formula 13]

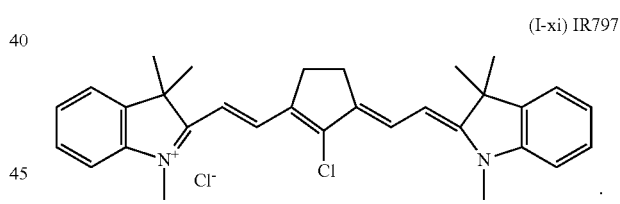

(I-xi) IR797

(15) The fluorescent nanoparticle probe according to any one of (1) to (4), wherein the fluorescent dye is represented by the following structural formula (I-xi):

[Chemical formula 14]

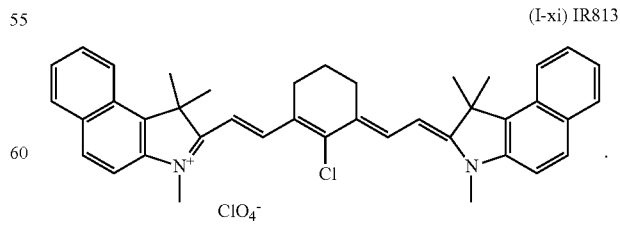

(I-xi) IR813

(16) The fluorescent nanoparticle probe according to any one of (1) to (15), wherein the hydrophobic block chain is selected from the group consisting of:

a hydrophobic polypeptide chain having 10 or more hydrophobic amino acid units, a hydrophobic polyester chain having 15 or more hydroxylic acid units, and a hydrophobic depsipeptide chain having a total of 20 or more units of both an amino acid unit and a hydroxylic acid unit.

(17) The fluorescent nanoparticle probe according to any one of (1) to (16), wherein the hydrophobic block chain is a hydrophobic block chain having 25 or more lactic acid units.

(18) A fluorescent molecular imaging method comprising the steps of:

administering the switching fluorescent nanoparticle probe according to anyone of (1) to (17) to a non-human animal; and detecting fluorescence.

Effects of the Invention

According to the present invention, it is possible to provide a novel fluorescent nanoparticle imaging probe having a switching function (i.e., a function to quench an encapsulated fluorescent dye during nanoparticle preparation, and emit fluorescence during imaging).

More specifically, according to the present invention, it is possible to provide a nanoparticle which encapsulates a cyanine-based fluorescent dye in a higher concentration than a conventional nanoparticle so that fluorescence of the encapsulated fluorescent dye is reduced dependently upon concentration (of the fluorescent dye) during preparation, and fluorescence is recovered dependently upon concentration (of a blood component) by contact with the blood component; said nanoparticle being excellent in accumulation in a desired tissue by EPR effect. Therefore, it is possible to provide a fluorescent nanoparticle probe that emits high-intensity fluorescence specifically in a desired tissue in a living body, and a fluorescence imaging method using the same.

BRIEF DESCRIPTION OF THE DRAWINGS

FIG. 2 shows the measurement results of fluorescence intensity of IC7-1-encapsulating lactosomes (1 mg/mL), wherein FIG. 2(a) shows the fluorescence maximum values of the lactosomes each encapsulating 0.5, 1, 2, 4, 8, 12, 16, and 20 mol % of IC7-1 measured at an excitation wavelength of 785 nm, and FIG. 2(b) shows the measurement results of fluorescence intensity converted per 1 µM concentration of the fluorescent dye.

MODES FOR CARRYING OUT THE INVENTION

[1. Amphiphilic Block Polymer]

Figure 1:
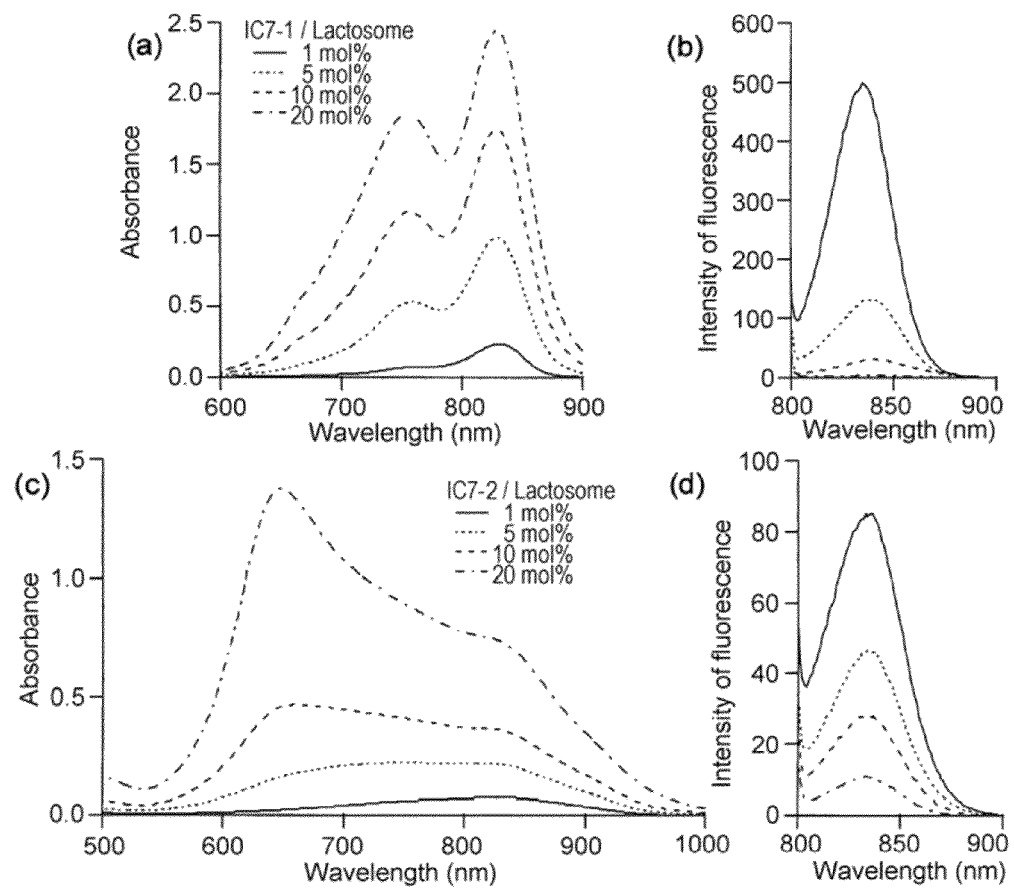
FIG. 1 shows the measurement results of absorption spectra (a) and (c) and fluorescence spectra (b) and (d) of lactosomes each encapsulating 1, 5, 10, and 20 mol % of IC7-1 or IC7-2.

An amphiphilic block polymer in the present invention has the following hydrophilic block and hydrophobic block. Hereinbelow, in the present invention, the term "amino acid" is used as a concept including natural amino acids, unnatural amino acids, and derivatives thereof by modification and/or chemical alteration. Further, in the specification, amino acids include α-, β-, and γ-amino acids. Among them, α-amino acids are preferred.

[1-1. Hydrophilic Block Chain]

In the present invention, the specific degree of the physical property "hydrophilicity" of a hydrophilic block chain is not particularly limited, but, at least, the hydrophilic block chain shall be hydrophilic enough to be a region relatively more hydrophilic than a specific hydrophobic block chain that will be described later so that a copolymer composed of the hydrophilic block chain and the hydrophobic block chain can have amphiphilicity as a whole molecule of the copolymer, or so that the amphiphilic block polymer can self-assemble in a solvent to form a self-assembly, preferably a particulate self-assembly.

The hydrophilic block chain is a hydrophilic molecular chain comprising, as an essential hydrophilic structural unit, a unit selected from the group consisting of a sarcosine-derived unit and an alkylene oxide- or alkylene glycol-derived unit, and having the 20 or more essential hydrophilic structural units. More specifically, the hydrophilic molecular chains include: a hydrophilic polypeptide chain having 20 or more, preferably 30 or more sarcosine units; a hydrophilic polyether chain having 20 or more alkylene oxide units; and a hydrophilic complex chain having a total of 20 or more, preferably 30 or more units of both a sarcosine unit and an alkylene oxide unit.

Sarcosine is N-methylglycine.

Specific examples of the alkylene oxide unit include an ethylene oxide unit (polyethylene glycol unit), a propylene oxide unit (propylene glycol), and the like. In the alkylene oxide unit, hydrogen may be substituted.

When the hydrophilic block chain has a structural unit other than the sarcosine unit and the alkylene oxide unit, such a structural unit is not particularly limited and examples thereof include amino acids other than sarcosine (including hydrophilic amino acids and other amino acids). Such amino acids are preferably α-amino acids. Examples of the α-amino acids include serine, threonine, lysine, aspartic acid, and glutamic acid.

In the hydrophilic block chain, the kind and ratio of the structural unit constituting the hydrophilic block chain are appropriately determined by those skilled in the art so that the block chain can have such hydrophilicity as described above as a whole.

The hydrophilic block chain can be designed so that the upper limit of the number of structural units is, for example, about 500. In the present invention, a hydrophilic block chain whose number of structural units is about 30 to 300, preferably about 50 to 200 may be often synthesized. If the number of structural units exceeds about 500, when a molecular assembly is formed, the resultant molecular assembly tends to be poor in stability. If the number of structural units is less than 30, formation of a molecular assembly tends to be difficult per se.

In the hydrophilic block chain, all the same structural units may be continuous or discontinuous. When the hydrophilic block chain contains another structural unit other than the above-described specific units, the kind and ratio of the another structural unit are appropriately determined by those skilled in the art so that the block chain can have the above-described hydrophilicity as a whole. In this case, molecular design is preferably performed so that basic characteristics that will be described later are not impaired.

Sarcosine (i.e., N-methylglycine) is highly water-soluble, and a sarcosine polymer has an N-substituted amide and therefore can be cis-trans isomerized as compared to a normal amide group, and has high flexibility due to less steric hindrance around the $C^{\alpha}$ carbon atom. The use of such a polypeptide as a structural block chain is very useful in that the block chain can have, as basic characteristics, both high hydrophilicity and high flexibility.

Further, a polyalkylene oxide chain is highly hydrophilic and has no adverse effects such as immunogenicity and toxicity. The use of such a polyether chain as a structural block chain is very useful in that the block chain can have, as basic characteristics, high hydrophilicity and the ability to reduce the antigenicity of a carrier agent and impart the carrier agent excellent stability and retainability in the blood.

[1-2. Hydrophobic Block Chain]

In the present invention, the specific degree of the physical property "hydrophobicity" of a hydrophobic block chain is not particularly limited, but, at least, the hydrophobic block chain shall be hydrophobic enough to be a region relatively more hydrophobic than the specific hydrophilic block chain so that a copolymer composed of the hydrophobic block chain and the hydrophilic block chain can have amphiphilicity as a whole molecule of the copolymer, or so that the amphiphilic block polymer can self-assemble in a solvent to form a self-assembly, preferably a particulate self-assembly.

The hydrophobic block chain is a hydrophobic molecular chain comprising, as an essential structural unit, a unit selected from the group consisting of an amino acid-derived structural unit and a hydroxylic acid-derived structural unit, and having the 20 or more essential structural units. More specifically, the hydrophobic molecular chains include: a hydrophobic polypeptide chain having 20 or more hydrophobic amino acid units; a hydrophobic polyester chain having 20 or more hydroxylic acid units; and a hydrophobic depsipeptide chain having a total of 20 or more units of both an amino acid unit and a hydroxylic acid unit.

The hydrophobic block chain in the present invention preferably has a helix structure.

Most of the hydrophobic amino acids have an aliphatic side chain, an aromatic side chain, and the like. Examples of natural amino acids include glycine, alanine, valine, leucine, isoleucine, proline, methionine, tyrosine, and tryptophan. Examples of unnatural amino acids include, but are not limited to, amino acid derivatives such as glutamic acid methyl ester, glutamic acid benzyl ester, aspartic acid methyl ester, aspartic acid ethyl ester, aspartic acid benzyl ester, and the like.

Examples of the hydroxylic acid include, but are not limited to, glycolic acid, lactic acid, hydroxyisobutyric acid, and the like.

In the hydrophobic block chain, the kind and ratio of the structural unit constituting the hydrophobic block chain are appropriately determined by those skilled in the art so that the block chain becomes hydrophobic as a whole.

The hydrophobic block chain can be designed so that the upper limit of the number of structural units is, for example, about 100. In the present invention, a hydrophobic block chain whose number of structural units is about 10 to 80, preferably about 20 to 50 may be often synthesized. If the number of structural units exceeds about 100, when a molecular assembly is formed, the resultant molecular assembly tends to be poor in stability. If the number of structural units is less than 10, formation of a molecular assembly tends to be difficult per se.

In the hydrophobic block chain, all the same structural units may be continuous or discontinuous. When the hydrophobic block chain contains another structural unit other than the above-described specific units, the kind and ratio of the another structural unit are appropriately determined by those skilled in the art so that the block chain can have the above-described hydrophobicity as a whole. In this case, molecular design is preferably performed so that basic characteristics that will be described later are not impaired.

The amino acid unit and the hydroxylic acid unit used in the hydrophobic block chain have excellent biocompatibility and stability. Therefore, a molecular assembly obtained from the amphiphilic substance having such polylactic acid as a structural block is very useful from the viewpoint of applicability to a living body, especially a human body.

Further, in particular, polylactic acid is rapidly metabolized due to its excellent biodegradability, and is therefore less likely to accumulate in tissue other than cancer tissue in a living body. Therefore, a molecular assembly obtained from the amphiphilic substance having such polylactic acid as a structural block is very useful from the viewpoint of specific accumulation in cancer tissue.

And, further, polylactic acid has excellent solubility in a low boiling point solvent, and therefore the use of a hazardous high boiling point solvent can be avoided when a molecular assembly is obtained from the amphiphilic substance having such polylactic acid as a structural block. Therefore, such a molecular assembly is very useful from the viewpoint of safety for a living body.

Furthermore, adjustment of the chain length of polylactic acid is preferred, in that the adjustment contributes, as one factor, to the control of the shape and size of a molecular assembly obtained from the amphiphilic substance having such polylactic acid as a structural unit. Therefore, the use of such a structural block is very useful from the viewpoint of the versatility of shapes of a resultant molecular assembly.

[1-3. Others]

In the present invention, the structural units constituting the amphiphilic block polymer may have another group. Such a group is appropriately selected by those skilled in the art and is not particularly limited. Example of the group includes functional groups such as an organic group having an appropriate chain length. Such a group may be used to allow the nanoparticle according to the present invention to have a form, a function and the like so that the nanoparticle becomes more useful as a molecular probe for, for example, a molecular imaging system or a drug delivery system, and is appropriately selected by those skilled in the art. Specific examples of the functional group include a sugar chain and a water-soluble polymer other than the above-described polyalkylene oxide chain. Examples of the sugar chain include carboxymethyl cellulose and amylose. Examples of the water-soluble polymer include a polyether chain and a polyvinyl alcohol chain.

[2. Fluorescent Dye]

In the present invention, a fluorescent dye encapsulated in a carrier agent is a cyanine compound represented by the following general formula (I).

[Chemical formula 15]

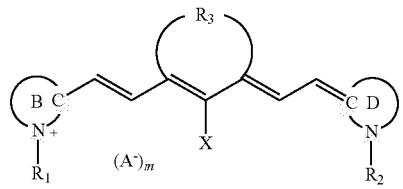

(I)

In the formula (I), $R_1$ and $R_2$ may be the same or different from each other and each is a hydrocarbon group which may be substituted.

Each of the hydrocarbon groups as $R_1$ and $R_2$ may be an alkyl group having 1 to 20 carbon atoms, preferably 2 to 5 carbon atoms. A substituent in each of $R_1$ and $R_2$ may be anionic, and may be a carboxyl group, a carboxylate group, a metal carboxylate group, a sulfonyl group, a sulfonate group, a metal sulfonate group, or a hydroxylic group. The metal may be an alkali metal or an alkaline earth metal.

Alternatively, each of the hydrocarbon groups as $R_1$ and $R_2$ may be a polylactic acid chain containing 5 to 50, preferably 15 to 35 lactic acid units. That is, in this case, the fluorescent dye that should be encapsulated is a fluorescently-labeled polylactic acid chain.

$R_3$ is a bivalent hydrocarbon group which may be substituted and which may have a cyclic structure. $R_3$ may be a group that has a cyclic structure to make the molecular structure of the fluorescent dye rigid. Preferred $R_3$ is an ethylene group or a propylene group.

X is a halogen, an aryloxy group, or a thioaryloxy group. The halogen may be Cl, Br, or I. The aryloxy group may be, for example, a phenoxy group. The thioaryloxy group may be, for example, a thiophenoxy group.

$A^-$ is an anion and m is 0 or 1. When m is 0, either $R_1$ or $R_2$ is an anionic group so that a molecule has a betaine structure as a whole. When m is 1, $A^-$ may be a halogen ion such as $Cl^-$, $Br^-$, or $I^-$; $ClO_4^-$, $BF_4^-$, $PF_6^-$, $BbF_6^-$, $SCN^-$ or the like.

The ring B and the ring D may be the same or different from each other and each is a nitrogen-containing bicyclic or tricyclic aromatic heterocycle. The ring B and the ring D are preferably the same.

Preferred examples of the ring B include the following structures.

[Chemical formula 16]

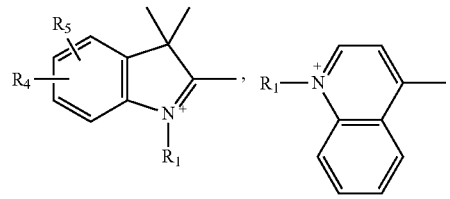

Preferred examples of the ring D include the following structures.

[Chemical formula 17]

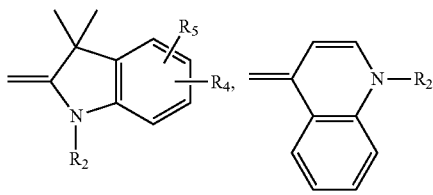

In the above formulas, both $R_4$ and $R_5$ may be hydrogen. Alternatively, $R_4$ and $R_5$ may be linked together to form an aryl ring. The aryl group may be a benzene ring which may be substituted.

In the present invention, the fluorescent dye is more preferably an indocyanine compound represented by the following structural formula (I-i).

[Chemical formula 18]

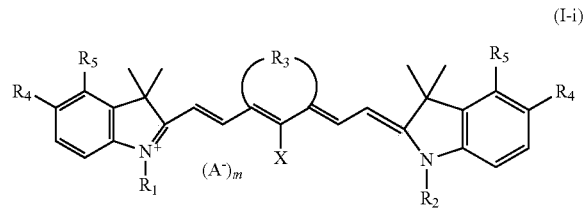

(I-i)

Specific examples of the fluorescent dye in the present invention include: IC7-1 (I-ii), IR820 (I-iii), and IR813 (I-xi) whose ring B and ring D are both nitrogen-containing tricyclic aromatic heterocycles; IR783 (I-iv), IR806 (I-v), IR775 (I-vii), IR780 (I-viii), IR792 (I-ix), and IR797 (I-x) whose ring B and ring D are both nitrogen-containing bicyclic aromatic heterocycles; and IC7-2 (I-vi) whose ring B is a nitrogen-containing tricyclic aromatic heterocycle and ring C is a nitrogen-containing bicyclic aromatic heterocycle. The structural formulas of these fluorescent dyes are shown below.

In the present invention, the fluorescent dyes include those in which at least a portion other than the N-substituted groups ($R_1$, $R_2$) has a symmetric structure as represented by, for example, the formula (I-ii), (I-iii), (I-iv), (I-v), (I-vii), (I-viii), (I-ix), (I-x), or (I-xi), and those having an asymmetric structure as represented by, for example, the formula (I-vi). In the present invention, the fluorescent dyes in which at least a portion other than the N-substituted groups has a symmetric structure are preferred. Among them, those represented by the formula (I-ii) have a symmetric structure in a portion other than the N-substituted groups, and those represented by the formula (I-iii), (I-iv), (I-v) (I-vii) (I-viii), (I-ix), (I-x), and (I-xi) have a symmetric structure in the molecule including the N-substituted groups as a whole.

[Chemical formula 19]

(I-ii) IC7-1

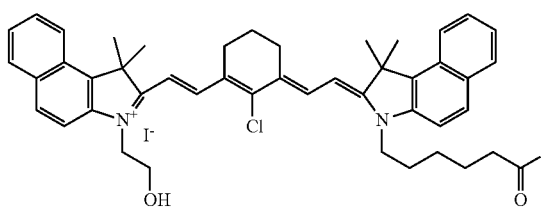

[Chemical formula 20]

(I-iii) IR820

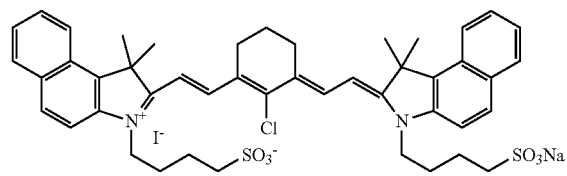

[Chemical formula 21]

(I-iv) IR783

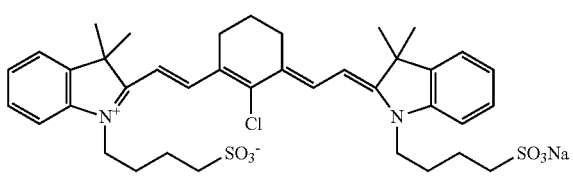

[Chemical formula 22]

(I-v) IR806

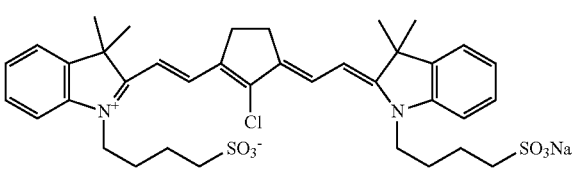

[Chemical formula 23]

(I-vi) IC7-2

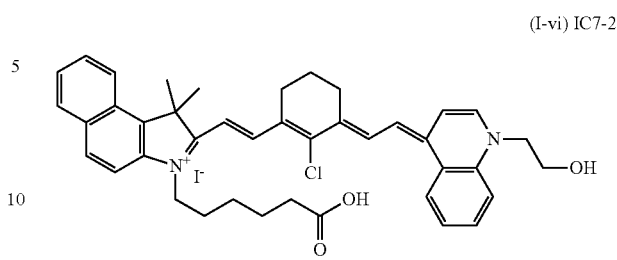

[Chemical formula 24]

(I-vii) IR775

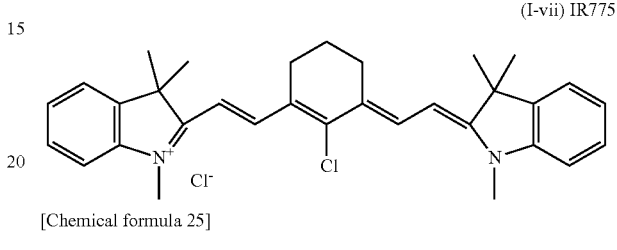

[Chemical formula 25]

(I-viii) IR780

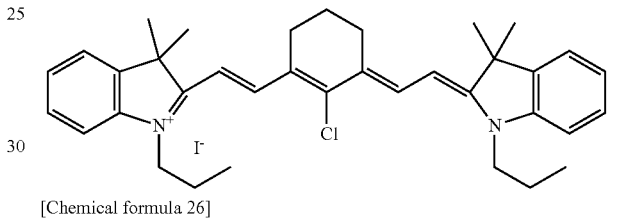

[Chemical formula 26]

(I-ix) IR792

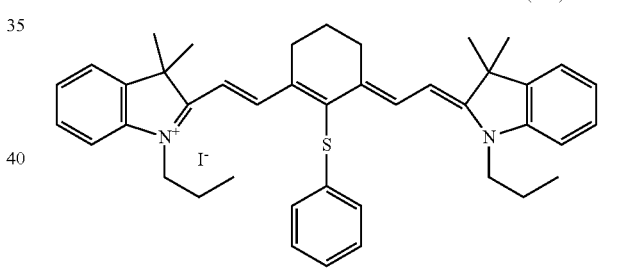

[Chemical formula 27]

(I-x) IR797

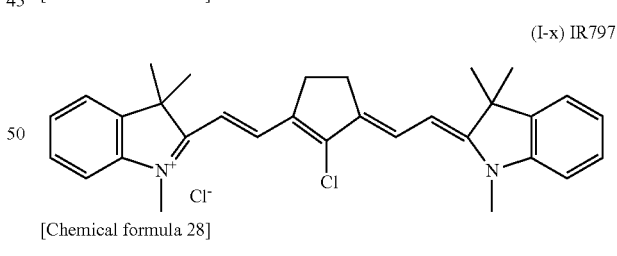

[Chemical formula 28]

(I-xi) IR813

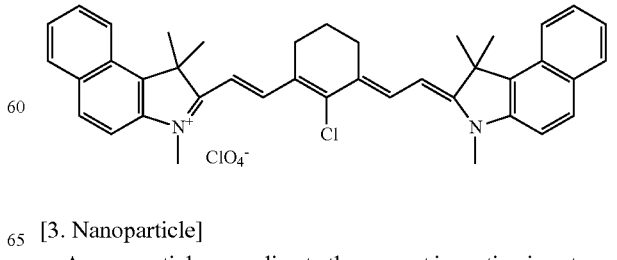

[3. Nanoparticle]

A nanoparticle according to the present invention is a structure in which the above-described fluorescent dye is encapsulated in a molecular assembly, as a carrier agent, that is formed by aggregation or self-assembling orientational association of the above-mentioned amphiphilic block polymer.

[3-1. Structure of Nanoparticle]

Figure 10:
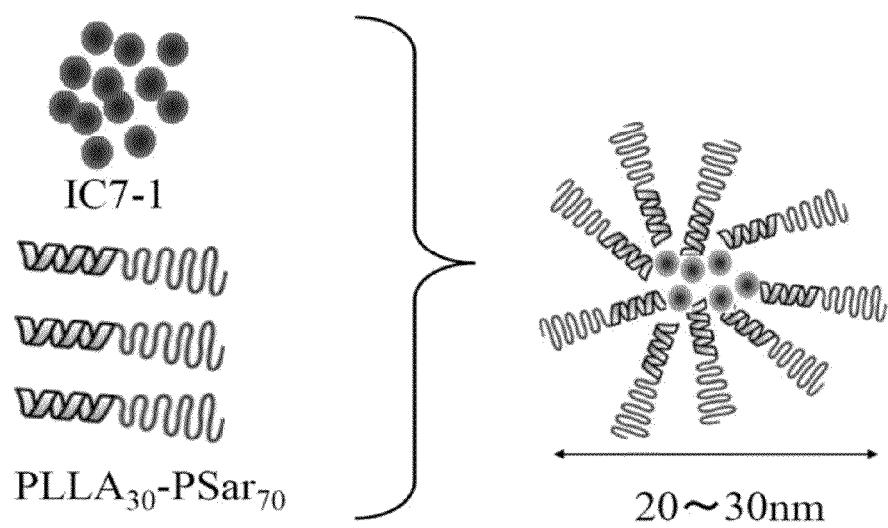
FIG. 10 shows a micelle (IC7-1 lactosome) formed by self-assembly from an amphiphilic block polymer (indicated as $PLLA_{30}$-$PSar_{70}$ in the drawing) and a fluorescent dye (indicated as IC7-1 in the drawing)

The molecular assembly in the present invention forms a micelle. One example of the micelle in the present invention is schematically shown in FIG. 10. FIG. 10 shows a micelle (IC7-1 lactosome) formed by self-assembly from an amphiphilic block polymer (illustrated as $PLLA_{30}$-$PSar_{70}$ in the drawing) and a fluorescent dye (illustrated as IC7-1 in the drawing).

As shown in FIG. 10, the amphiphilic block polymer self-assembles so that a hydrophobic block chain forms a core portion. On the other hand, the fluorescent dye is located in the hydrophobic core portion. At this time, the fluorescent dye that is a cyanine-based dye is associated. Therefore, fluorescence is quenched (i.e., in an off-state that will be described later).

The molecular assembly that is a carrier agent of the nanoparticle according to the present invention can achieve, in an on-state that will be described later, both flexibility that allows the nanoparticle to respond to its external environment and encapsulation stability that allows the fluorescent dye to be held by the molecular assembly.

[3-2. Amount of Fluorescent Dye Encapsulated in Nanoparticle]

The nanoparticle according to the present invention encapsulates two or more molecules of the fluorescent dye per single nanoparticle. For example, the amount of the fluorescent dye may be 1 to 50 mol % with respect to the total amount of the amphiphilic block polymer and the fluorescent dye. The amount of the fluorescent dye may be preferably 5 to 20 mol %, or 10 to 20 mol %. In the present invention, 1 mol % of the fluorescent dye with respect to the total amount of the amphiphilic block polymer and the fluorescent dye generally corresponds to two molecules of the fluorescent dye encapsulated in the single nanoparticle. If the amount of the fluorescent dye is less than the above range, the nanoparticle tends to be unable to have a switching function, and if the amount of the fluorescent dye exceeds the above range, formation of the nanoparticle tends to be difficult.

[3-3. Switching Function of Nanoparticle]

[3-3-1. Off Function]

The nanoparticle according to the present invention encapsulates two or more molecules of the fluorescent dye. The encapsulated two or more molecules are self-quenched by their association.

The degree of quenching depends on the amount of the encapsulated fluorescent dye. That is, the intensity of fluorescence per certain amount of the fluorescent dye exponentially reduces as the amount of the encapsulated fluorescent dye increases. The degree of the reduction may vary depending on the fluorescent dye. When the intensity of fluorescence is measured at an amphiphilic polymer concentration of $1/15$ mg/mL, there is a case where the intensity of fluorescence converted per certain amount (e.g., 1 μM) of the fluorescent dye is reduced to ½ every time the amount of the encapsulated fluorescent dye increases by 1.12 to 2.07 mol %. An example of the case where the intensity of fluorescence may be reduced to ½ every time the amount of the encapsulated fluorescent dye increases by 1.12 mol % is a case where the intensity of fluorescence is measured when the concentration of lactosomes (molecular assemblies composed of a polysarcosine-polylactic acid amphiphilic block polymer and functioning as carrier parts of the nanoparticles) encapsulating IC7-1 is adjusted to the above-described value. A quenching ratio determined by comparison with the intensity of fluorescence measured when the amount of the encapsulated fluorescent dye is 0.5 mol % (corresponding to one molecule of the fluorescent dye per single nanoparticle) is 1/1.36 to $1/1.95 \times 10^{13}$ at the maximum (i.e., in the case where fluorescence intensity is reduced to ½ every time the amount of the fluorescent dye increases by 1.12 mol %) when the amount of the encapsulated fluorescent dye is 1 to 50 mol % (corresponding to 2 to 200 molecules of the fluorescent dye per single nanoparticle); or the quenching ratio is 1/355 to $1/1.72 \times 10^5$ at the maximum when the amount of the encapsulated fluorescent dye is 10 to 20 mol % (corresponding to 22 to 50 molecules of the fluorescent dye per single nanoparticle).

Therefore, the nanoparticle according to the present invention can be efficiently quenched even when the number of fluorescent molecules is small.

The quenching state (off-state) as described above is maintained in at least an environment during nanoparticle preparation. The environment in which the off-state is maintained may be any environment as long as an on-state that will be described later is not caused. Examples of such an environment include a water-based environment, such as water or an aqueous solution containing no surfactant and no blood component, and an anhydrous environment. The water or aqueous solution may be any water or aqueous solution as long as it is biochemically or pharmaceutically acceptable, and specific examples thereof include distilled water for injection, normal saline, and a buffer solution. A preferred example thereof includes phosphate buffered saline. The nanoparticle in an anhydrous environment refers to a freeze-dried nanoparticle.

[3-3-2. On Function]

The nanoparticle in the above-described off-state responds to a change in its outer environment, and is put into a state where the nanoparticle recovers fluorescence (i.e., an on-state).

An environment causing the on-state is not particularly limited as long as the fluorescent dye encapsulated in the nanoparticle can be dissociated. Such an environment where the fluorescent dye can be dissociated is considered as an environment having the effect of deforming the structure of the molecular assembly as a carrier agent. Further, the environment is preferably an environment where the structure of the carrier agent can be deformed to dissociate the fluorescent dye, while the dissociated fluorescent dye can continue to be held by the nanoparticle without being released from the nanoparticle. This makes it possible to cause a preferred on-state.

A specific example of a component contained in the environment causing the on-state is a blood component.

Examples of the blood component include blood, plasma, serum, and albumin.

The blood component can cause the on-state as long as its concentration is at a level in an in vivo environment. For example, when the blood component is albumin, the on-state can be caused at a concentration of the blood component in the range of 0.5 to 10 wt %, or a concentration 2.3 to 47 times higher (molar basis) than that of the encapsulated fluorescent dye. When the concentration is less than the above range, the intensity of fluorescence does not tend to be sufficiently recovered, and on the other hand, when the concentration exceeds the above range, the intensity of fluorescence tends to reach a ceiling due to maximum fluorescence recovery. It is to be noted that the degree of fluorescence recovery changes depending on the concentration of the blood component, which has been confirmed by the present inventors.

When being put into the on-state, the nanoparticle recovers fluorescence that has been quenched during the off-state. The intensity of fluorescence after recovery may vary depending on the kind of carrier agent or encapsulated fluorescent dye, but may be larger than the intensity of fluorescence during the off-state (e.g., during a state in which the nanoparticle is present in phosphate buffered saline). Although the following is merely one example, when the amount of the encapsulated fluorescent dye is 1 to 50 mol % (corresponding to 2 to 200 molecules of the fluorescent dye per single nanoparticle), the intensity of fluorescence may be about 1.09 to 2,200 times higher at the maximum; or when the amount of the encapsulated fluorescent dye is 10 to 20 mol % (corresponding to 22 to 50 molecules of the fluorescent dye per single nanoparticle), the intensity of fluorescence may be about 45.2 to 287 times higher at the maximum. In the present invention, the intensity of fluorescence after recovery is preferably 10 times or more higher than the intensity of fluorescence during the off-state. More preferably, the intensity of fluorescence is 100 times or more higher. The upper limit of the above range is not particularly limited and is, for example, 10,000 times.

[3-4. Size of Nanoparticle]

[3-4-1. Size of Nanoparticle]

For example, the nanoparticle according to the present invention has a particle size of 10 to 500 nm. Here, the "particle size" refers to a particle diameter that appears at the highest frequency in a particle size distribution, that is, a median particle diameter. When the particle size is smaller than 10 nm, it is difficult to form the nanoparticle. On the other hand, when the particle size exceeds 500 nm, there is a case where, particularly when administered to a living body by injection, the nanoparticles are not suitable for use in an injection.

[3-4-2. Measurement of Nanoparticle Size]

A method for measuring the size of the nanoparticle according to the present invention is not particularly limited, and is appropriately selected by those skilled in the art. Examples of such a method include an observation method using a transmission electron microscope (TEM) and a dynamic light scattering (DLS) method. In the DLS method, the translational diffusion coefficient of a particle undergoing Brownian movement in a solution is measured.

[3-4-3. Control of Nanoparticle Size]

An example of a means for controlling the size of the molecular assembly is the control of chain length of the amphiphilic block polymer. Preferably, adjustment of the degree of polymerization of the hydrophobic block in the amphiphilic block polymer is effective.

[3-5. Formation of Nanoparticle]

A method for forming the nanoparticle is not particularly limited, and can be appropriately selected by those skilled in the art depending on the desired size and characteristics of the nanoparticle; the kind, properties and content of the fluorescent dye to be carried; or the like. If necessary, after nanoparticles are formed in the following manner, the obtained nanoparticles may be subjected to surface modification by a known method.

It is to be noted that the confirmation of formation of particles may be performed by electron microscope observation.

[3-5-1. Film Method]

A film method is a method that has been used for liposome preparation. The amphiphilic block polymer in the present invention has solubility in a low boiling point solvent, and therefore the nanoparticle can be prepared by this method.

The film method comprises the following steps of: preparing a solution, in a container (e.g., a glass container), containing the amphiphilic block polymer and the fluorescent dye in an organic solvent; removing the organic solvent from the solution to obtain, on an inner wall of the container, a film containing the amphiphilic block polymer and the fluorescent dye; and adding water or an aqueous solution to the container, and performing ultrasonic treatment or warming treatment to convert the film-shaped substance into molecular assemblies encapsulating the fluorescent dye to obtain a dispersion liquid of nanoparticles. Further, this film method may comprise the step of subjecting the dispersion liquid of nanoparticles to freeze-drying treatment.

The solution containing the amphiphilic block polymer and the fluorescent dye in an organic solvent may be prepared by previously preparing a film comprising the amphiphilic block polymer, and then adding a solution containing the fluorescent dye at the time of nanoparticle preparation to the film for dissolution.

The organic solvent to be used in the film method is preferably a low boiling point solvent. In the present invention, the low boiling point solvent refers to a solvent whose boiling point at 1 atmospheric pressure is 100° C. or lower, preferably 90° C. or lower. Specific examples of the low boiling point solvent include chloroform, diethyl ether, acetonitrile, ethanol, acetone, dichloromethane, tetrahydrofuran, hexane, and the like.

The use of such a low boiling point solvent to dissolve the amphiphilic block polymer and the fluorescent dye makes it very easy to perform solvent removal. A method for solvent removal is not particularly limited, and may be appropriately determined by those skilled in the art depending on the boiling point of an organic solvent to be used, or the like. For example, solvent removal may be performed under reduced pressure, or by natural drying.

After the organic solvent is removed, a film containing the amphiphilic block polymer and the fluorescent dye is formed on the inner wall of the container. Water or an aqueous solution is added to the container to which the film is attached. The water or aqueous solution is not particularly limited, and biochemically or pharmaceutically acceptable ones may be appropriately selected by those skilled in the art. Examples thereof include distilled water for injection, normal saline, and a buffer solution.

After water or an aqueous solution is added, warming treatment is performed. The film is peeled off from the inner wall of the container by warming, and in this process, molecular assemblies are formed. The warming treatment can be performed under the conditions of, for example, 70 to 100° C. and 5 to 60 minutes. After the completion of the warming treatment, a dispersion liquid in which molecular assemblies (nanoparticles) encapsulating the fluorescent dye are dispersed in the water or aqueous solution is prepared in the container.

The obtained dispersion liquid can be directly administered to a living body. That is, the nanoparticles do not need to be stored by themselves under solvent-free conditions.

On the other hand, the obtained dispersion liquid may be subjected to freeze-drying treatment. A method for freeze-drying treatment is not particularly limited, and any known method can be used. For example, the dispersion liquid of nanoparticles obtained in such a manner as described above may be frozen by liquid nitrogen, or the like, and sublimated under reduced pressure. In this way, freeze-dried product of the nanoparticles is obtained. That is, the nanoparticles can be stored as a freeze-dried product. If necessary, water or an aqueous solution may be added to the freeze-dried product to obtain a dispersion liquid of nanoparticles, and the nanoparticles can be used. The water or aqueous solution is not particularly limited, and biochemically or pharmaceutically acceptable ones may be appropriately selected by those skilled in the art. Examples thereof include distilled water for injection, normal saline, and a buffer solution.

Here, the dispersion liquid before freeze-drying treatment may contain, in addition to the nanoparticles according to the present invention formed from the amphiphilic block polymer and the fluorescent dye, the amphiphilic block polymer and/or the fluorescent dye remaining per se without contributing to the formation of such nanoparticles. By subjecting such a dispersion liquid to freeze-drying treatment, in the process of concentration of a solvent, it is possible to further form nanoparticles from the amphiphilic block polymer and the fluorescent dye remaining without forming the nanoparticles according to the present invention. Therefore, preparation of the nanoparticles according to the present invention can be efficiently performed.

[3-5-2. Injection Method]

An injection method is a method used for preparation of not only the nanoparticle according to the present invention but also many other nanoparticles. In this method, an amphiphilic block polymer and a fluorescent dye are dissolved in an organic solvent such as trifluoroethanol, ethanol, hexafluoroisopropanol, dimethylsulfoxide, or the like to obtain a solution; and the solution is dispersed in a water-based solvent such as distilled water for injection, normal saline, or a buffer solution and subjected to purification treatment such as gel filtration chromatography, filtering, or ultracentrifugation; and then the organic solvent is removed to prepare nanoparticles. When nanoparticles obtained in this way using an organic solvent hazardous to a living body are administered to a living body, the organic solvent needs to be strictly removed.

[4. Fluorescent Molecular Imaging Method]

A fluorescent molecular imaging method according to the present invention comprises administering the above-described fluorescent nanoparticle to a living body as a probe. The fluorescent molecular imaging method according to the present invention is characterized by using the above-described fluorescent probe, and other specific procedures can be appropriately determined by those skilled in the art according to a known fluorescent molecular imaging method.

[4-1. Administration of Fluorescent Probe]

A living body to which the fluorescent probe is administered is not particularly limited, and may be a non-human animal. The non-human animal is not particularly limited, and may be a mammal other than a human. Specific examples thereof include primates, gnawing mammals (e.g., mice, rats), rabbits, dogs, cats, pigs, bovines, sheep, and horses.

A method for administration to a living body is not particularly limited, and can be appropriately determined by those skilled in the art. Therefore, the administration method may be either systemic or local as long as the fluorescent probe can come into contact with a blood component. That is, the administration of the molecular probe can be performed by any one of injection (needle injection or needleless injection), oral administration, and external application.

The fluorescent probe according to the present invention has a switching function. Therefore, fluorescence is quenched after preparation of the fluorescent probe and before administration to a living body, but the fluorescent probe emits fluorescence when brought into contact with a blood component by administration to a living body.

[4-2. Administration Target]

The nanoparticle used as a fluorescent probe in the method according to the present invention is excellent in specific accumulation in a vascular lesion site (e.g., a malignant tumor site, an inflammatory site, an arterial sclerosis site, an angiogenic site). The fluorescent probe according to the present invention accumulates in the tissue of such a site due to EPR (enhanced permeability and retention) effect, and therefore its accumulation does not depend on the kind of tissue of a vascular lesion site. The administration target of the fluorescent probe according to the present invention is preferably a cancer. Examples of the cancer as the administration target include a wide variety of cancers such as liver cancers, pancreas cancers, lung cancers, uterine cervical cancers, breast cancers, and colon cancers.

[4-3. Detection of Fluorescent Probe]

A molecular imaging system according to the present invention comprises the step of detecting fluorescence derived from an administered fluorescent probe. By detecting the administered fluorescent probe, it is possible to observe the states of an administration target (especially, the position and size of tissue such as a cancer) from outside the body.

As a detection method, any means that can visualize the administered fluorescent probe can be used. The detection means can be appropriately determined by those skilled in the art depending on the kind of fluorescent dye contained in the fluorescent probe.

For example, irradiation of a living body, to which the fluorescent probe has been administered, with excitation light makes it possible to detect fluorescence emitted from the fluorescent dye contained in the fluorescent probe in the body.

Parameters such as an excitation wavelength and a fluorescence wavelength to be detected can be appropriately determined by those skilled in the art depending on the kind of fluorescent dye contained in the fluorescent probe to be administered and the kind of administration target.

The time from administration to the start of detection can be appropriately determined by those skilled in the art depending on the kind of fluorescent dye contained in the fluorescent probe to be administered and the kind of administration target. For example, detection may be started after a lapse of 3 to 48 hours from administration. If the time is shorter than the above range, a detected signal is too strong and therefore it tends to be difficult to clearly distinguish an administration target from other sites (background). On the other hand, if the time is longer than the above range, the fluorescent probe tends to be excreted from the administration target.

From the viewpoint of accuracy, the fluorescent probe is preferably detected by measurement of a living body not from one direction but from two or more directions. More specifically, the measurement is preferably performed from at least three directions, more preferably at least five directions. When measurement is performed from five directions, a living body can be measured from, for example, both right and left abdomen sides, both right and left sides of the body, and the back side.

EXAMPLES

Hereinbelow, the present invention will be described in more detail with reference to examples.

In the examples, nanoparticles according to the present invention were prepared using a polysarcosine-polylactic acid amphiphilic block polymer (PSar-PLLA), a polyethylene glycol-polylactic acid amphiphilic block polymer (PEG-PLLA), or polysarcosine-poly(leucine-aminoisobutyric acid) (PSar-P(Leu-Aib)) as a carrier agent, and a fluorescent compound IC7-1, IC7-2, IR820 (Aldrich), IR783 (Aldrich), or IR806 (Aldrich) as a fluorescent dye encapsulated in the carrier agent. However, the present invention is not limited to these examples.

Further, nanoparticles for comparison purposes were prepared using the above-described polysarcosine-polylactic acid amphiphilic block polymer (PSar-PLLA) as a carrier agent, and a fluorescent compound ICG (Sigma), Rhodamine 800 (Sigma), Rhodamine 101 (Sigma), or Rhodamine 6G (Aldrich) as a fluorescent dye encapsulated in the carrier agent.

The structures of the fluorescent compounds are shown below.
[Chemical formula 29]
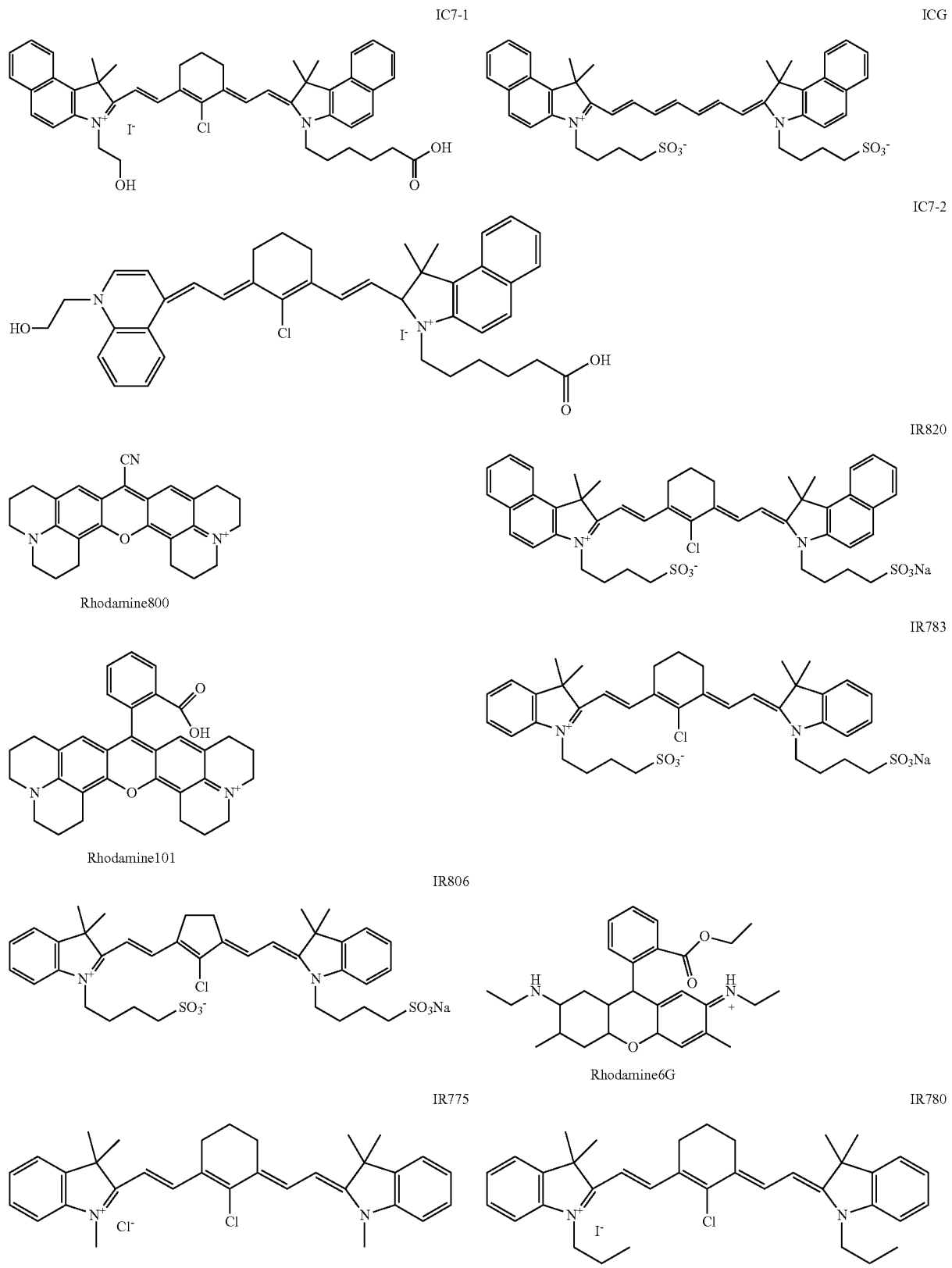

-continued

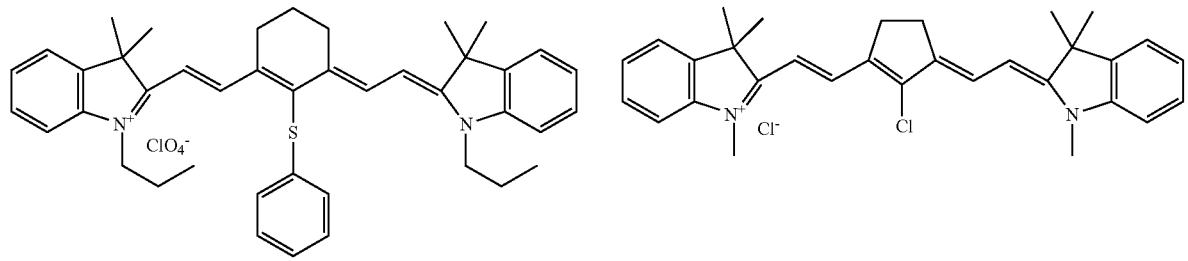

IR792

IR797

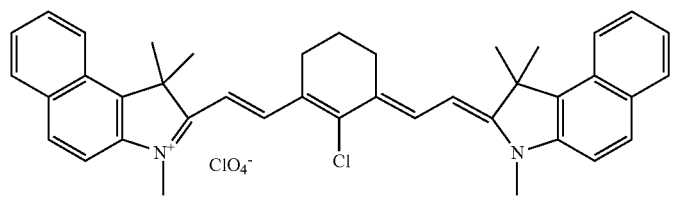

IR813

Experimental Example 1

Synthesis of N-[5-Anilino-3-chloro-2,4-(propane-1,3-diyl)-2,4-pentadiene-1-ylidene]anilinium Chloride (compound 1)

Anhydrous DMF (13 mL, 0.17 mol) was placed in a 100 mL three-necked flask and cooled to 0° C. Phosphorous oxychloride (11 mL, 0.12 mol) was dropped thereinto for 15 minutes. After stirring at 0° C. for 1 hour, cyclohexanone (5.5 mL, 0.053 mol) was added. After stirring at room temperature for 1 hour, heating to reflux was performed and stirring was further performed for 1 hour. After cooling to room temperature, 18 mL of a mixed solution of aniline/EtOH=1/1 (volume ratio) was added. After 30 minutes, 110 mL of a mixed solution of $H_2O$/HCl=10/1 (volume ratio) was added and allowed to stand at 5° C. overnight. A precipitate was collected by filtration and washed with THF and cold water to give crystals, and the resultant crystals were dried with $P_2O_5$ in a desiccator to obtain a compound 1 (Scheme 1). A yield of 53.6% (10.2 g) was achieved.

Scheme 1

[Chemical formula 30]

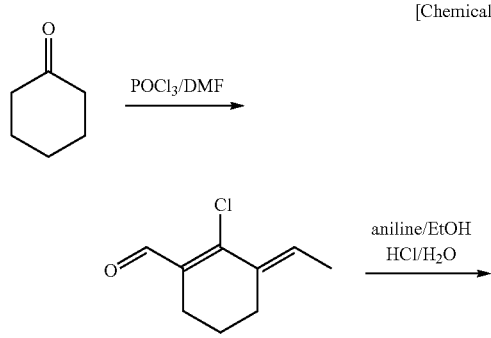

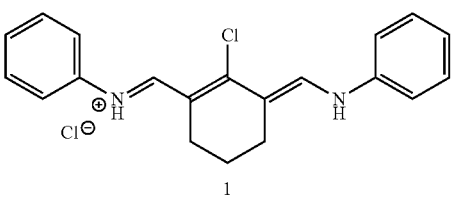

1

Experimental Example 2

Synthesis of 3-(5-Carboxy-pentyl)-1,1,2-trimethyl-1H-benzo[e]indolium; iodide (compound 2)

To a 50 mL eggplant flask, 6-Bromohexanoic Acid (8.4 g, 43.0 mmol), potassium iodide (7.2 g, 43 mmol), and 5 mL of toluene were added, and then 1,1,2-Trimethyl-1H-benzo[e]indole (3.0 g, 14.3 mmol) was added. After heating to reflux was performed for 15 hours, a precipitated solid was collected by filtration. The solid was washed with THF, cold water, and chloroform in this order, and dried in a desiccator to obtain a compound 2 (Scheme 2). A yield of 77% (5.0 g) was achieved.

Scheme 2

[Chemical formula 31]

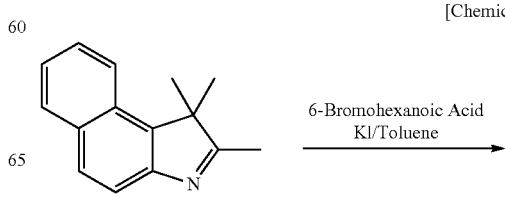

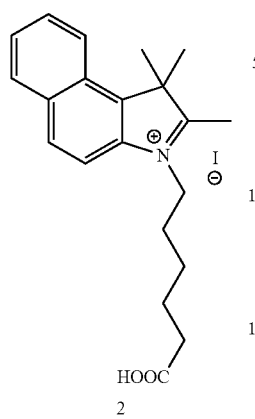

2

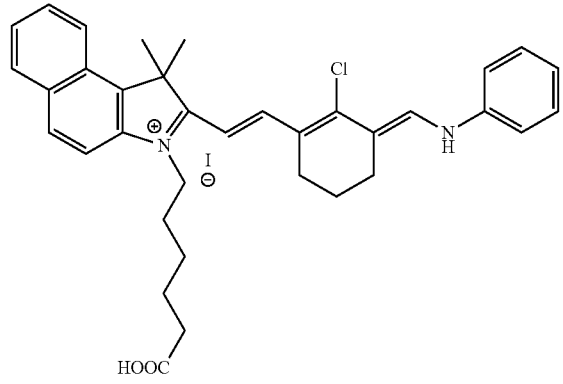

3

Experimental Example 3

Synthesis of Intermediate 3

The compound 1 (3.00 g, 8.35 mmol), the compound 2 (3.77 g, 8.35 mmol), and anhydrous sodium acetate (0.753 g, 9.19 mmol) were dissolved in 75.0 mL of anhydrous ethanol, and heated to reflux under a nitrogen atmosphere for 6 hours. After the completion of reaction, a 0.2 mol/L phosphate buffer solution (pH=7.0) was added for neutralization, and then an organic substance was extracted with chloroform. The extract was once concentrated, and then purified by column chromatography to obtain an intermediate 3 (Scheme 3). A yield of 25.5% (1.45 g) was achieved.

Experimental Example 4

Synthesis of 3-(2-Hydroxy-ethyl)-1,1,2-trimethyl-1H-benzo[e]indolium; iodide (compound 4)

To a 50 mL three-necked flask, 1,1,2-Trimethyl-1H-benzo[e]indole (2.0 g, 9.556 mmol) and 10 mL of anhydrous toluene were added, and heated to 80° C. under a nitrogen atmosphere. After the 1, 1,2-Trimethyl-1H-benzo[e]indole was completely dissolved in the toluene, 2-Iodoethanol (1.64 g, 9.556 mmol) was added. After heating to reflux was performed for 2 hours, cooling to room temperature was performed and precipitated pale blue crystals were collected by filtration. The crystals were washed with toluene, and dried in a desiccator to obtain a compound 4 (Scheme 4). A yield of 33% (1.21 g) was achieved.

Scheme 3

[Chemical formula 32]

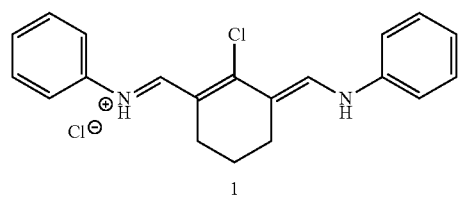

+

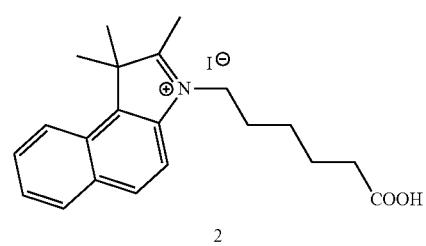

$\xrightarrow{\text{NaOAc/dry EtOH}}$

Scheme 4

[Chemical formula 33]

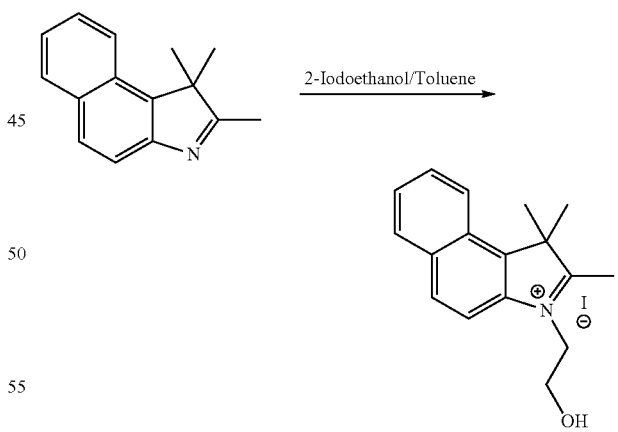

Experimental Example 5

Synthesis of IC7-1

The intermediate 3 (1.16 g, 1.70 mmol), the compound 4 (0.714 g, 1.87 mmol), and anhydrous sodium acetate (0.153 g, 1.87 mmol) were dissolved in 29.0 mL of anhydrous ethanol, and heated to reflux under a nitrogen atmosphere for 5 hours. After the completion of reaction, a 0.2 mol/L phosphate buffer solution (pH=7.0) was added for neutralization, and then an organic substance was extracted with chloroform. The extract was once concentrated, and then purified by column chromatography to obtain IC7-1 (Scheme 5). A yield of 85.3% (1.22 g) was achieved.

Scheme 5

[Chemical formula 34]

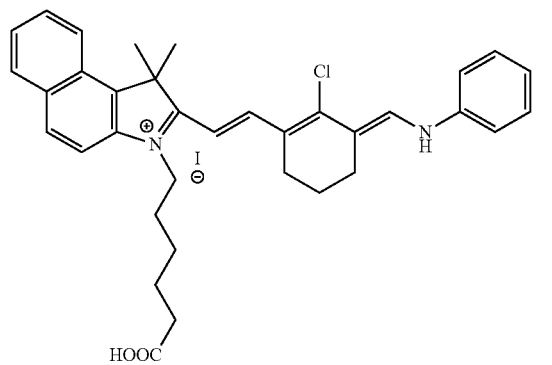

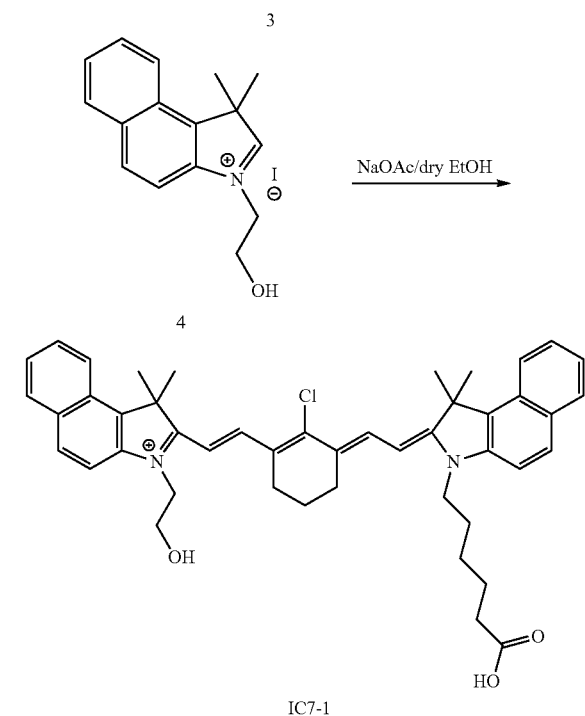

IC7-1

Experimental Example 6

Synthesis of 1-(2-Hydroxy-ethyl)-4-methyl-quinolinium; iodide (compound 5)

To a 50 mL eggplant flask, 4-Methylquinoline (1 g, 7 mmol) and 2-Iodoethanol (1.2 g, 7 mmol) were added and dissolved in 4 mL of toluene. After heating and stirring for 5 hours, yellow crystals were collected by filtration, washed with toluene, and then dried in a desiccator to obtain a compound 5 (Scheme 6). A yield of 74% (1.63 g) was achieved.

Scheme 6

[Chemical formula 35]

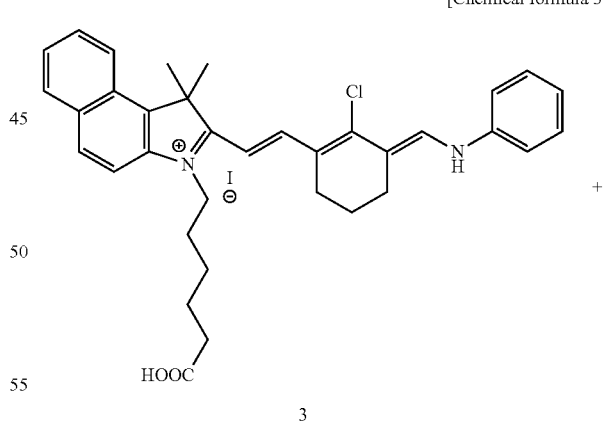

Experimental Example 7

Synthesis of IC7-2

The intermediate 3 (414.0 mg, 0.608 mmol), the compound 5 (210.7 mg, 0.669 mmol), and anhydrous sodium acetate (54.9 mg, 0.669 mmol) were dissolved in 12.0 mL of anhydrous ethanol, and heated to reflux under a nitrogen atmosphere for 8 hours.

After the completion of reaction, a 0.2 mol/L phosphate buffer solution (pH=7.0) was added for neutralization, and then an organic substance was purified by liquid separating operation using chloroform/methanol/water to obtain IC7-2 (Scheme 7). A yield of 46.7% (221 mg) was achieved.

Scheme 7

[Chemical formula 36]

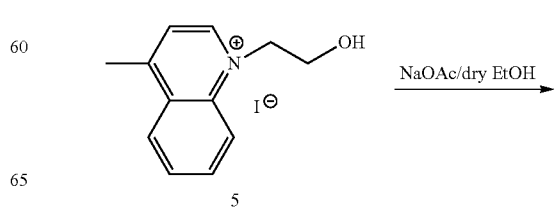

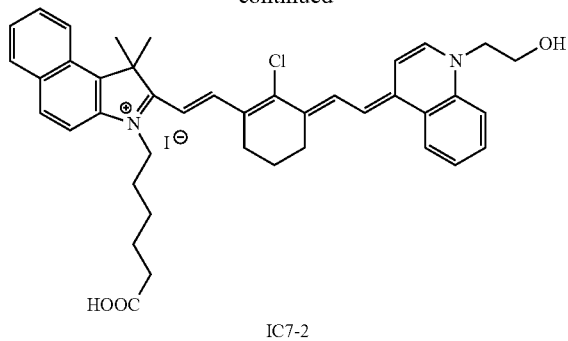

IC7-2

Experimental Example 8

Synthesis of polysarcosine-polylactic acid amphiphilic block polymer (PSar$_{70}$-PLLA$_{30}$)

In this experimental example, a polysarcosine-polylactic acid amphiphilic block polymer (PSar$_{70}$-PLLA$_{30}$) was synthesized from sarcosine-NCA (Sar-NCA) and aminated poly-L-lactic acid (a-PLA) (Scheme 12).

Scheme 12

[Chemical formula 37]

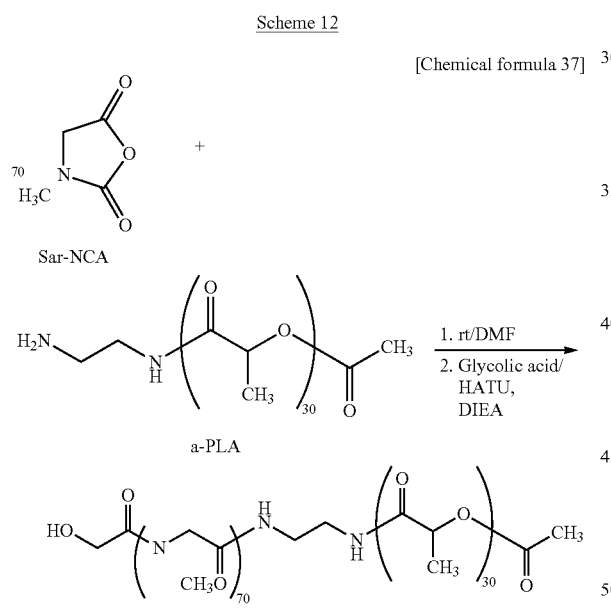

Dimethylformamide (DMF) (140 mL) was added to a-PLA (383 mg, 0.17 mmol) and sarcosine-NCA (Sar-NCA) (3.21 g, 27.9 mmol) under an Ar atmosphere, and the mixture was stirred at room temperature for 12 hours. After the reaction solution was cooled to 0° C., glycolic acid (72 mg, 0.95 mmol), O-(benzotriazol-1-yl)-N,N,N',N'-tetramethyluronium hexafluorophosphate (HATU) (357 mg, 0.94 mmol), and N,N-diisopropylethylamine (DIEA) (245 μL, 1.4 mmol) were added to the reaction solution, and reaction was performed at room temperature for 18 hours.

After DMF was distilled away under reduced pressure by a rotary evaporator, purification was performed using an LH20 column. Fractions showing a peak detected at UV 270 nm were collected and concentrated. The thus obtained concentrated solution was dropped into diethyl ether at 0° C. for reprecipitation to obtain PSar$_{70}$-PLLA$_{30}$ (1.7 g) as a target substance.

Experimental Example 9

Synthesis of polyethylene glycol-polylactic acid amphiphilic block polymer (PEG-PLLA)

To a DMF solution containing a-PLA (0.47 g, 206 μmol) dissolved therein, 1.1 molar equivalents of SUNBRIGHT ME-050AS (NOF Corporation) was added, and the mixture was stirred under an argon gas atmosphere at 30° C. overnight. After the completion of reaction, the obtained solution was concentrated to about 5.0 mL, and purified on a gel filtration column (Sephadex LH-20, DMF elution). The absorbance of fractions was measured at a wavelength of 270 nm to detect a target polymer. Each of the collected solutions was concentrated and dropped into diethyl ether cooled in ice, and a white precipitate was collected by centrifugation. A yield of 48% (0.71 g) was achieved.

Scheme 13

[Chemical formula 38]

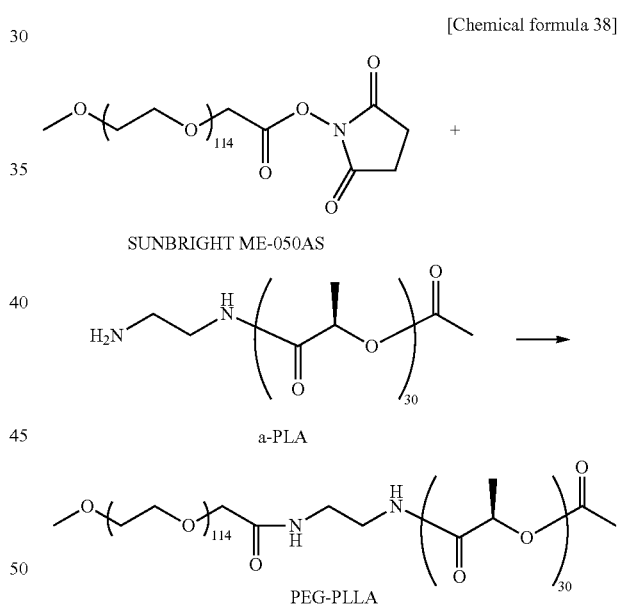

Experimental Example 10

Synthesis of polysarcosine-poly(leucine-aminoisobutyric acid) (PSar-P(Leu-Aib))

In this experimental example, an amphiphilic substance, sarcosine-poly(leucine-aminoisobutyric acid) (PSar-P(Leu-Aib)) was synthesized from sarcosine-NCA (Sar-NCA) and poly(leucine-aminoisobutyric acid) (P(Leu-Aib)) (Scheme 14).

31

Scheme 14

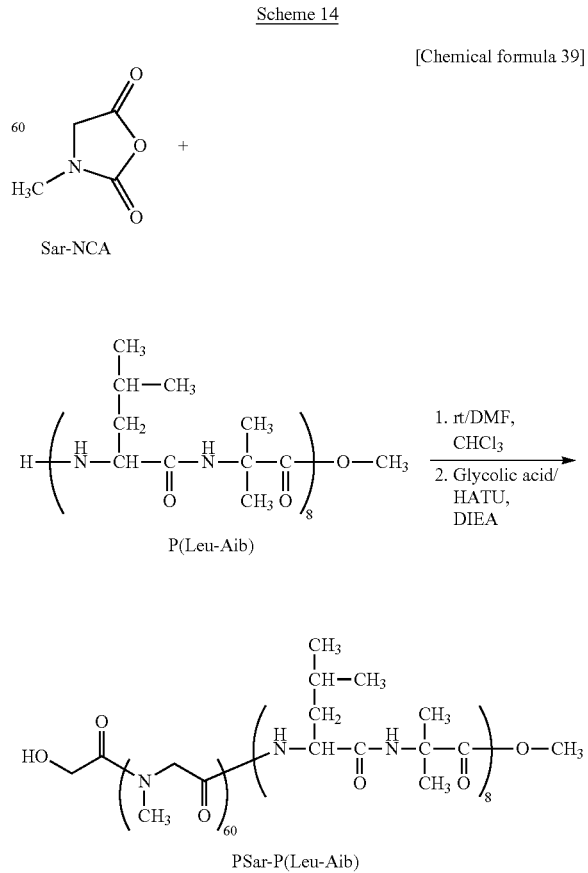

[Chemical formula 39]

Boc-(Leu-Aib)$_8$-OMe (600 mg, 0.349 mmol) was added to a mixed solution of 6.0 mL of trifluoroacetic acid (TFA) and 0.6 mL of anisole, and removal of Boo group was performed to obtain a TFA salt derivative. The TFA salt derivative was wasged with isopropyl ether, and dried under vacuum for 2 hours to obtain a dried product. The dried product was dissolved in chloroform and neutralized with a 4 wt % aqueous sodium hydrogen carbonate solution to perform removal of TFA group. The chloroform solution was concentrated to obtain 420 mg (0.259 mmol) of poly(leucine-aminoisobutyric acid) (P(Leu-Aib)).

The obtained P(Leu-Aib) was dissolved in 8.0 mL of a 1/1 (v/v) mixed solution of DMF and HCl$_3$, and the mixed solution was added to 6.0 mL of a 1/1 (v/v) mixed solution of DMF and HCl$_3$ containing Sar-NCA (1.11 g, 15.6 mmol) dissolved therein. After the Sar-NCA was consumed by reaction, the reaction solution was cooled to 0° C., and glycolic acid (98 mg, 1.30 mmol) HATU (492 mg, 1.30 mmol), and DIEA (338 μL, 1.94 mmol) were added thereto, and stirred at room temperature for 10 hours. Further, glycolic acid (40 mg, 0.52 mmol), HATU (198 mg, 0.52 mmol), and DIEA (135 μL, 0.78 mmol) were added to the reaction solution, and the reaction solution was stirred for 12 hours. After the completion of reaction, the reaction solution was concentrated and subjected to gel filtration using Sephadex LH-20 to purify a target product PSar-P(Leu-Aib) (186 mg).

32

Example 1

Production of Nanoparticles Encapsulating Fluorescent Dye

Example 1-1

Production of Lactosomes Encapsulating Fluorescent Dye

A molecular assembly that is a carrier part of a nanoparticle and is composed of a polysarcosine-polylactic acid amphiphilic block polymer is referred to as a lactosome.

In this example, lactosomes encapsulating, as a fluorescent dye, IC7-1, IC7-2, ICG (for comparison), IR820 (Aldrich), IR783 (Aldrich), IR806 (Aldrich), Rhodamine 800 (Sigma) (for comparison), Rhodamine 101 (Sigma) (for comparison), or Rhodamine 6G (Aldrich) (for comparison) were prepared.

A chloroform solution (0.2 mM) of a polylactic acid-polysarcosine amphiphilic block polymer (PSar$_{70}$-PLLA$_{30}$.26H$_2$O, MW=7,767) as a carrier agent, and a chloroform solution (0.2 mM) of each of the above-mentioned fluorescent dyes were prepared. Both the solutions were mixed in a glass container so that the molarity of the fluorescent dye was 0.5 mol % (for comparison), 1 mol %, 2 mol %, 4 mol %, 5 mol %, 8 mol %, 10 mol %, 12 mol %, 16 mol %, or 20 mol %, respectively. Then, the solvent was distilled away under reduced pressure to form a film containing the carrier agent and the fluorescent dye on the wall surface of the glass container. Further, water or a buffer solution was added to the glass container having the film formed therein, and the glass container was put in hot water at 82° C. for 20 minutes and was then allowed to stand at room temperature for 30 minutes, and the water or buffer solution was filtered with a 0.2 mm filter and freeze-dried.

Example 1-2

Production of PEG-PLLA Encapsulating Fluorescent Dye

In this example, nanoparticles encapsulating IC7-1 as a fluorescent dye were prepared using a polyethylene glycol-polylactic acid amphiphilic block polymer (PEG-PLLA) as a carrier agent.

Three mg of a polyethylene glycol-polylactic acid amphiphilic block polymer (PEG$_{114}$-PLLA$_{30}$, MW=7,302) and 20 mol % (103 nmol) of IC7-1 were dissolved in 0.1 mL of acetonitrile to obtain a solution, and then the solution was added to 1.9 mL of ultrapure water with stirring to form particles. The obtained particle-containing solution was subjected to solvent exchange with 3 mL of ultrapure water using a gel filtration column (PD-10, GE Healthcare) to obtain a solution containing PEG-PLLA particles encapsulating IC7-1.

Example 1-3

Production of Peptosomes (PSar-P(Leu-Aib)) Encapsulating Fluorescent Dye

A molecular assembly that is a carrier part of a nanoparticle and is composed of polysarcosine-poly(leucine-aminoisobutyric acid) is referred to as a peptosome.

In this example, a peptosome encapsulating IC7-1 as a fluorescent dye was prepared.

Three mg of a polysarcosine-poly(leucine-aminoisobutyric acid) amphiphilic block polymer (PSar$_{60}$-P(Leu-Aib)$_8$, MW=6,001) and 20 mol % (125 nmol) of IC7-1 were dissolved in 0.1 mL of ethanol to obtain a solution, and then the solution was added to 1.9 mL of ultrapure water with stirring to form particles. The obtained particle-containing solution was subjected to solvent exchange with 3 mL of ultrapure water using a gel filtration column (PD-10, GE Healthcare) to obtain a solution containing peptosome particles encapsulating IC7-1.

Example 2

Absorption and Fluorescence Spectra of Lactosome Encapsulating Fluorescent Dye

Among the lactosomes encapsulating the fluorescent dye IC7-1 (IC7-1/Lactosomes) obtained in Example 1-1, the freeze-dried products of the lactosomes each encapsulating 1 mol %, 5 mol %, 10 mol % and 20 mol % of the fluorescent dye were subjected to measurement of absorption spectra and fluorescence spectra in the following manner.

The measurement of absorption spectra was performed to confirm that each of these lactosomes encapsulated the fluorescent dye according to their respective fluorescent dye blend ratios. Further, the measurement of fluorescence intensity of the fluorescent dye-encapsulating lactosomes was performed. The measurement of absorption spectra was performed using an ultraviolet-visible spectrophotometer (UVmini-1240, manufactured by SHIMADZU CORPORATION). The measurement of fluorescence spectra was performed at an excitation wavelength of 785 nm in the range of 700 to 900 nm using a fluorescence spectrophotometer (RF-5300PC, manufactured by SHIMADZU CORPORATION).

Each of the fluorescent dye-encapsulating lactosomes was dispersed in ultrapure water so that the concentration of the amphiphilic polymer was 1 mg/mL to measure absorption and fluorescence spectra (FIG. 1). The lactosome encapsulating 1 mol % of IC7-1 had adsorption maximum at 831 nm and fluorescence maximum at 836 nm. Although the intensity of absorbance increased as the fluorescent dye content increased, the intensity of fluorescence was highest when the fluorescent dye content was 1 mol %, and was reduced to about 1/120 when the fluorescent dye content was 20 mol % as compared to when the fluorescent dye content was 1 mol % (FIGS. 1(a) and 1(b)). The lactosome encapsulating 1 mol % of IC7-2 had absorption maximum at 831 nm and fluorescence maximum at 833 nm. IC7-2 had a wider absorption spectrum than IC7-1. Also when IC7-2 was contained, quenching of fluorescence was observed. The intensity of fluorescence was reduced to about 1/8 when the IC7-2 content was 20 mol % as compared to when the IC7-2 content was 1 mol % (FIGS. 1(c) and 1(d)).

Example 3

Intensity of Fluorescence of Lactosome Encapsulating IC7-1

Figure 2:
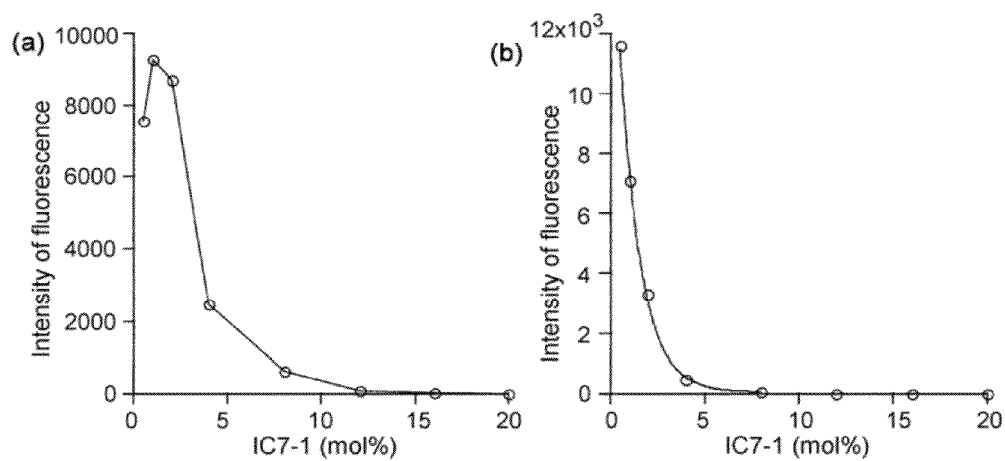

Among the lactosomes encapsulating the fluorescent dye IC7-1 (IC7-1/Lactosomes) obtained in Example 1-1, the lactosomes each encapsulating 0.5 mol % (for comparison), 1 mol %, 2 mol %, 4 mol %, 8 mol %. 12 mol %, 16 mol %, or 20 mol % of the fluorescent dye IC7-1 (IC7-1/Lactosomes) were dispersed in ultrapure water so that the concentration of the amphiphilic polymer was 1 mg/mL to measure the maximum value of fluorescence at an excitation wavelength of 785 nm (FIG. 2(a)). As a result, it was found that the intensity of fluorescence was highest when the IC7-1 content was 1 mol %. The intensity of fluorescence converted per 1 μM concentration of the fluorescent dye had a tendency to exponentially reduce and to be reduced to ½ every time the fluorescent dye content increased by 0.78 mol % until the fluorescent dye content reached 8 mol % (FIG. 2(b)).

Example 4

Comparison of Fluorescence Intensity of IC7-1-Encapsulating Particle Between Before and after Change in External Environment As described above, it has become apparent that fluorescence quenching occurs in the lactosome (IC7-1/Lactosome) in which IC7-1 is encapsulated in the carrier agent PSar-PLLA at a high density. Requirements for recovery of fluorescence intensity under in vivo conditions were studied. A water dispersion of the lactosome encapsulating 20 mol % of IC7-1 in a carrier agent PSar-PLLA (1 mg/mL) and phosphate buffered saline (PBS), plasma (collected from a male ddY), 5 wt % albumin (BSA), or 5 wt % SDS were mixed 1:1 (volume ratio), respectively, and the mixture was allowed to stand at room temperature for 30 minutes under lightproof conditions, and then diluted with PBS so that the concentration of the amphiphilic polymer was 1/15 mg/mL to measure a fluorescence spectrum (FIG. 3(a)).

Figure 3:
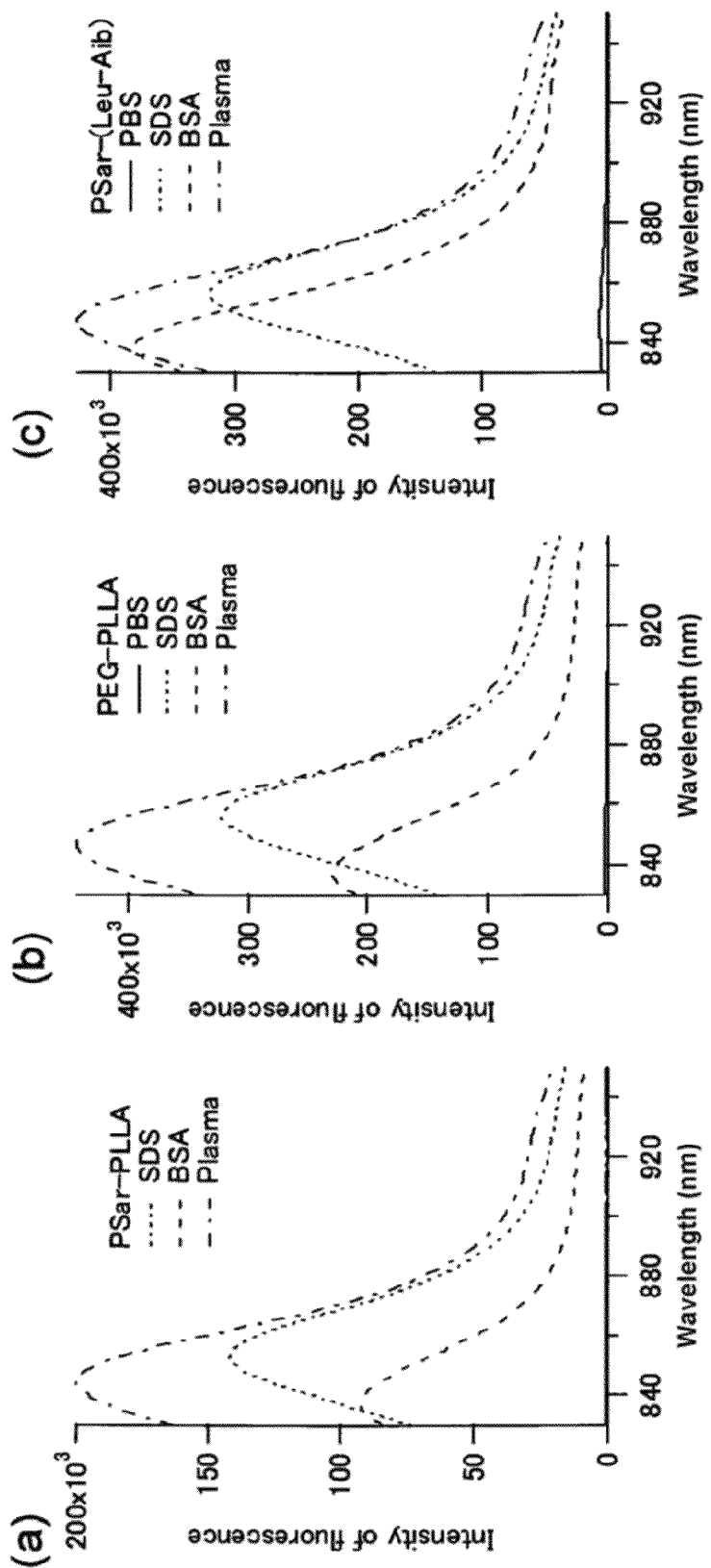
FIG. 3 shows the measurement results of fluorescence spectra when PBS, SDS, BSA, or plasma was added to lactosomes (PSar-PLLA), PEG-PLLA particles (PEG-PLLA), and peptosomes (PSar-P(Leu-Aib)) encapsulating 20 mol % of IC7-1, respectively.

Similarly, the particles encapsulating 20 mol % of IC7-1 in a carrier agent PEG-PLLA, and the peptosome encapsulating 20 mol % of IC7-1 in a carrier agent PSar-P(Leu-Aib) were also subjected to measurement of fluorescence spectra, respectively (FIGS. 3(b) and 3(c)).

It is to be noted that specific composition of the phosphate buffered saline (PBS) is as follows: 29 g of $Na_2HPO_4.12H_2O$, 2.96 g of $NaH_2PO_4.2H_2O$, and 8.7 g of NaCl per 1 liter of ultrapure water.

A comparison of the ratio of fluorescence intensity before and after change in external environment (addition of plasma) among the nanoparticles encapsulating 20 mol % of IC7-1 is shown in Table 1 described below.

TABLE 1

| Amphiphilic polymer | Fluorescence maximum (nm) | Fluorescence intensity (A) | Fluorescence intensity (PBS)(B) | Ratio of fluorescence intensity (A/B) |
|---|---|---|---|---|
| PSar-PLLA | 844 | 199746 | 696 | 287.0 |
| PSar-P(Leu-Aib) | 847 | 427131 | 6679 | 64.0 |
| PEG-PLLA | 847 | 444177 | 2672 | 166.2 |

A comparison of the ratio of fluorescence intensity before and after change in external environment (addition of 5 wt % BSA) among the nanoparticles encapsulating 20 mol % of IC7-1 is shown in Table 2 described below.

TABLE 2

| Amphiphilic polymer | Fluorescence maximum (nm) | Fluorescence intensity (A) | Fluorescence intensity (PBS)(B) | Ratio of fluorescence intensity (A/B) |
|---|---|---|---|---|
| PSar-PLLA | 837 | 92384 | 591 | 156.3 |
| PSar-P(Leu-Aib) | 838 | 382596 | 5894 | 64.9 |
| PEG-PLLA | 837 | 229913 | 2478 | 92.8 |

A comparison of the ratio of fluorescence intensity before and after change in external environment (addition of 5 wt % SDS) among the nanoparticles encapsulating 20 mol % of IC7-1 is shown in Table 3 described below.

TABLE 3

| Amphiphilic polymer | Fluorescence maximum (nm) | Fluorescence intensity (A) | Fluorescence intensity (PBS)(B) | Ratio of fluorescence intensity (A/B) |
|---|---|---|---|---|
| PSar-PLLA | 852 | 141929 | 694 | 204.5 |
| PSar-P(Leu-Aib) | 857 | 320539 | 5642 | 56.8 |
| PEG-PLLA | 856 | 322970 | 2209 | 146.2 |

In all the cases, the IC7-1-encapsulating lactosome had the highest ratio of fluorescence intensity in SDS, BSA, or plasma to that in PBS at the fluorescence maximum wavelength (Tables 1 to 3). Particularly, the fluorescence intensity that recovered in plasma was 287 times the fluorescence intensity in PBS. Further, in all the cases, there was a tendency that the lactosome had the highest fluorescence intensity ratio, followed by the PEG-PLLA particle and the peptosome (Tables 1 to 3). The hydrophobic part of the lactosome or the PEG-PLLA particle is composed of polylactic acid having a $3_{10}$ helix structure, and the hydrophobic core of the peptosome is composed of an amino acid-based polymer having an α-helix structure. From this, it is considered that when the hydrophobic part of the nanoparticle has a helix structure, quenching of a cyanine-based fluorescent dye and recovery of fluorescence intensity by a change in its external environment are observed.

Example 5

Comparison of Ratio of Fluorescence Intensity Before and after Change in External Environment Among Fluorescent Dye-Encapsulating Lactosomes One hundred μL of a water dispersion of the lactosomes containing 20 mol % of IC7-1, ICG (for comparison), IR820, IR783, IR806, Rhodamine 800 (for comparison), Rhodamine 101 (for comparison), Rhodamine 6G (for comparison), IR775, IR780, IR792, IR797, or IR813 (1 mg/mL) or 100 μL of a water dispersion of the lactosome containing 15 mol % of IC7-2 (1 mg/mL); and 100 μL of PBS, plasma (collected from a ddY mouse), 5 wt % BSA (solvent: PBS), or 5 wt % SDS (solvent: PBS) were mixed, and the mixture was stirred at room temperature for 30 minutes under lightproof conditions, and then diluted with PBS so that the concentration of the amphiphilic polymer was 1/15 mg/mL to measure a fluorescence spectrum using Fluorolog-3 (HORIBA Jobin Yvon Inc.). The results of measurement are shown in FIGS. 4(a) to 4(f), FIGS. 5(j) to 5(l), and FIGS. 11(m) to 11(q).

Figure 4:
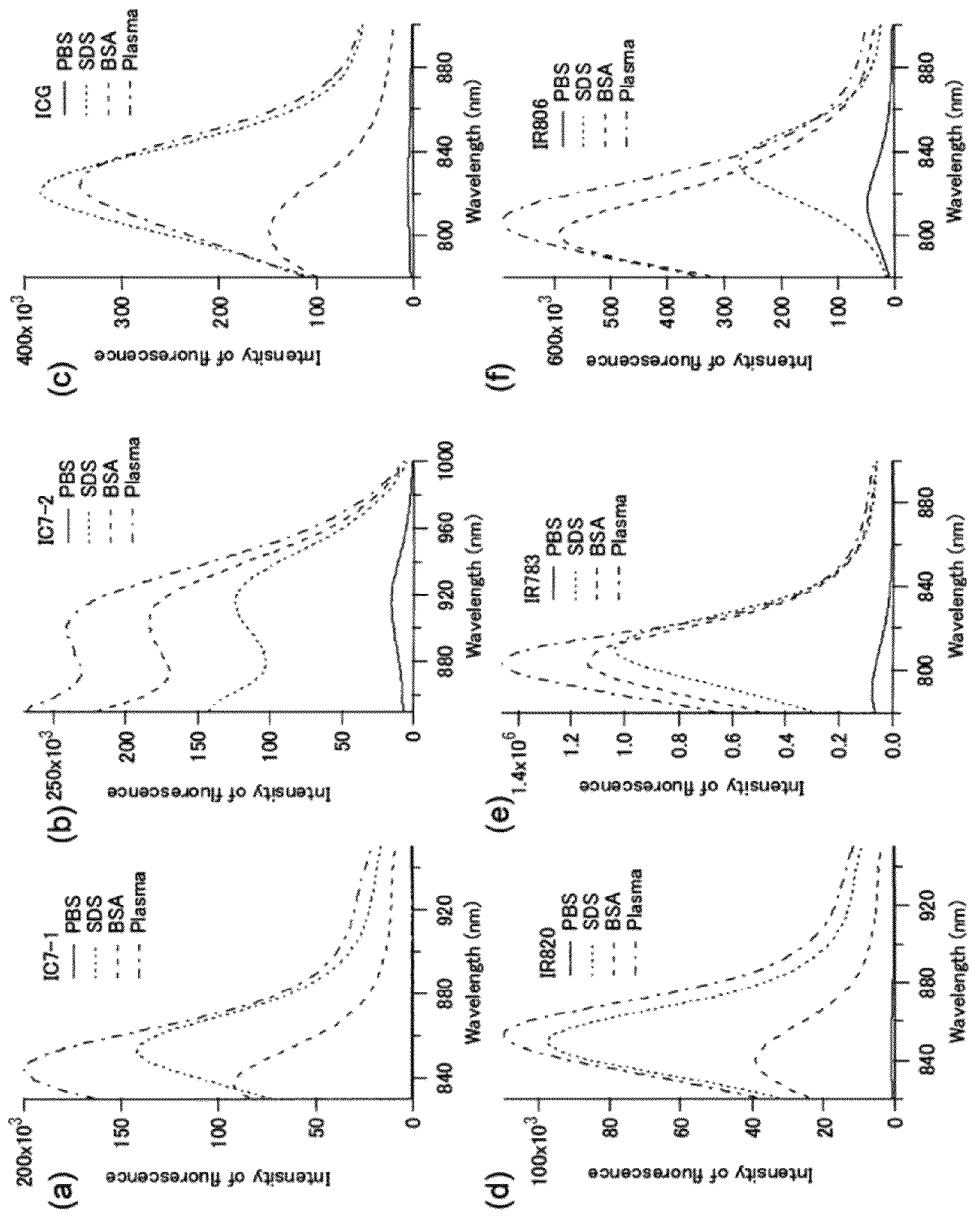
FIG. 4 shows the measurement results of fluorescence spectra when PBS, SDS, BSA, or plasma was added to lactosomes encapsulating a fluorescent dye (IC7-1 (a), IC7-2 (b), ICG (c), IR820 (d), IR783 (e), or IR806(f)).
Figure 5:
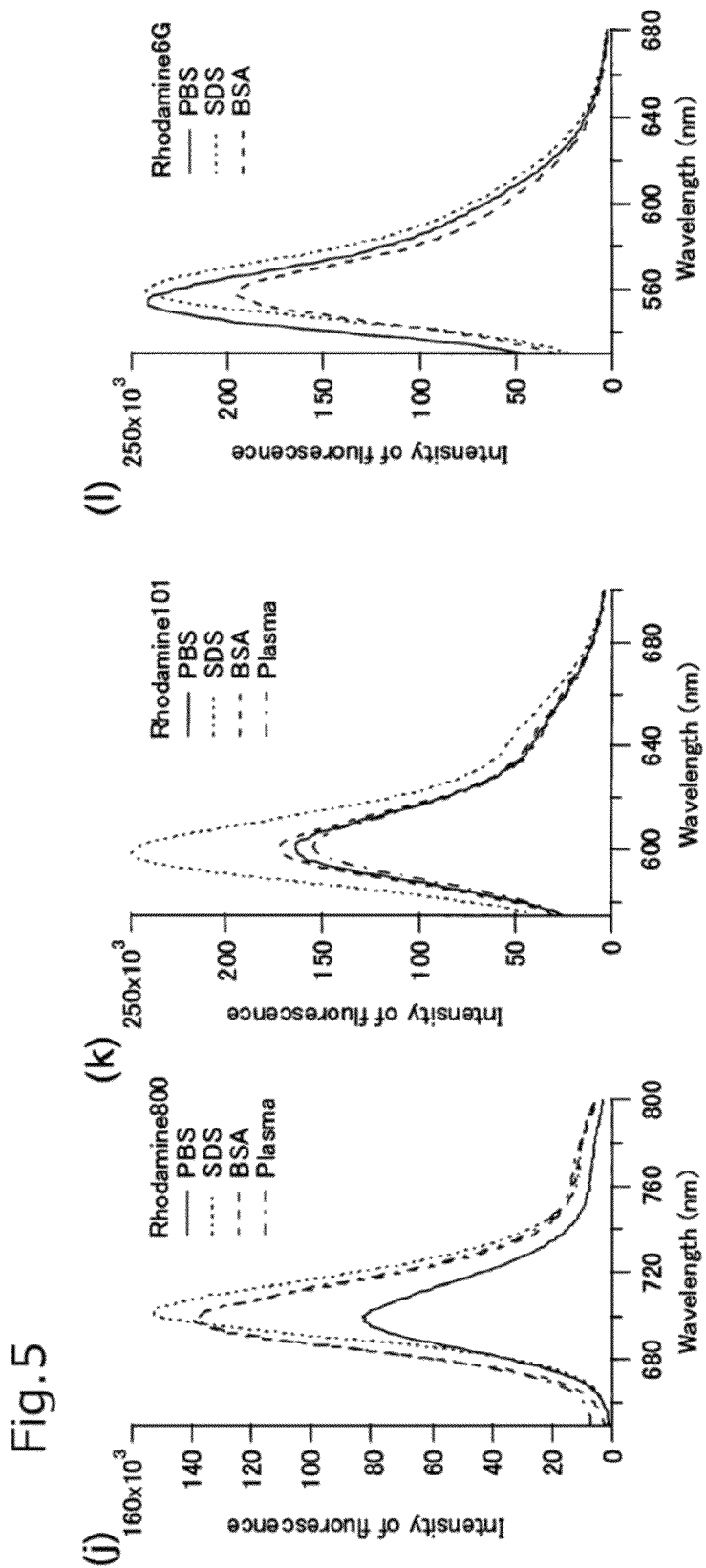
FIG. 5 shows the measurement results of fluorescence spectra when PBS, SDS, BSA, or plasma was added to lactosomes encapsulating a fluorescent dye (Rhodamine-800 (j), Rhodamine-101 (k), or Rhodamine-6G (l)).
Figure 11:
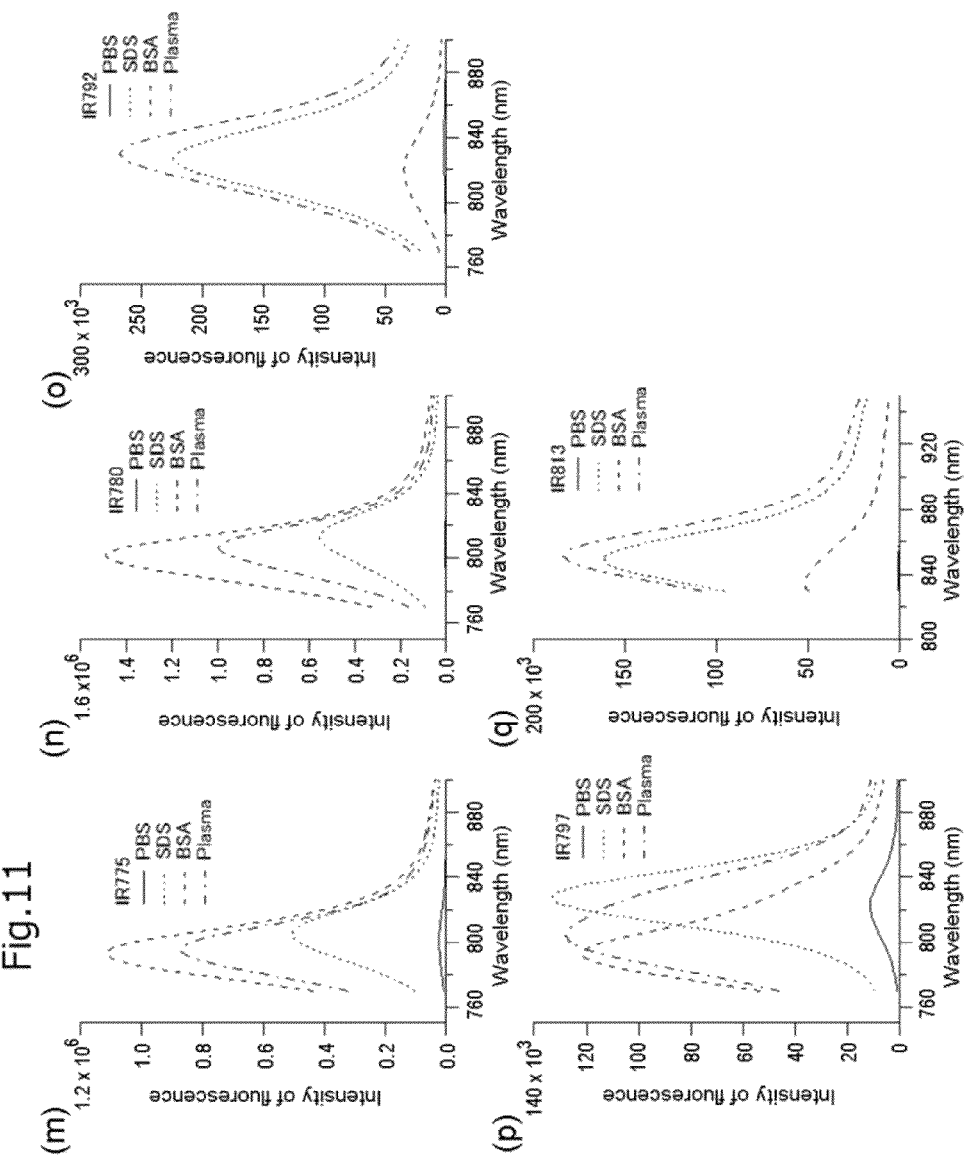
FIG. 11 shows the measurement results of fluorescence spectra when PBS, SDS, BSA, or plasma was added to lactosomes encapsulating a fluorescent dye (IR775 (m), IR780 (n), IR792 (o), IR797 (p), or IR813 (q)).

As a result, in the cases of the lactosomes encapsulating a cyanine-based fluorescent dye, the intensity of fluorescence was markedly increased by mixing with plasma or BSA as compared to the intensity of fluorescence in the PBS solution (FIGS. 4 and 11). In contrast, in the cases of the lactosomes encapsulating a fluorescent dye having a rhodamine skeleton, a remarkable recovery of fluorescence intensity was not observed (FIGS. 5(j) to 5(l)).

A comparison of the ratio of fluorescence intensity before and after change in external environment (addition of plasma) among the fluorescent dye-encapsulating lactosomes is shown in Table 4 described below.

TABLE 4

| Dye | Fluorescence maximum (nm) | Fluorescence intensity (A) | Fluorescence intensity (PBS)(B) | Ratio of fluorescence intensity (A/B) |
|---|---|---|---|---|
| IC7-1 | 844 | 199746 | 696 | 287.0 |
| IC7-2 | 901 | 241880 | 14224 | 17.0 |
| ICG | 824 | 342590 | 5212 | 65.7 |
| IR820 | 852 | 109922 | 1025 | 107.2 |
| IR783 | 803 | 1460710 | 63974 | 22.8 |
| IR806 | 806 | 693318 | 42632 | 16.3 |
| Rhodamine 800 | 699 | 138170 | 82260 | 1.7 |
| Rhodamine 101 | 601 | 154280 | 163410 | 0.9 |

A comparison of the ratio of fluorescence intensity before and after change in external environment (addition of 5 wt % BSA) among the fluorescent dye-encapsulating lactosomes is shown in Table 5 described below.

TABLE 5

| Dye | Fluorescence maximum (nm) | Fluorescence intensity (A) | Fluorescence intensity (PBS)(B) | Ratio of fluorescence intensity (A/B) |
|---|---|---|---|---|
| IC7-1 | 837 | 92384 | 591 | 156.3 |
| IC7-2 | 903 | 185345 | 14147 | 13.1 |
| ICG | 802 | 148650 | 4454 | 33.4 |
| IR820 | 841 | 39046 | 1079 | 36.2 |
| IR783 | 804 | 1144532 | 62207 | 18.4 |
| IR806 | 801 | 591322 | 36395 | 16.2 |
| Rhodamine 800 | 699 | 139250 | 82260 | 1.7 |
| Rhodamine 101 | 600 | 171710 | 163500 | 1.1 |
| Rhodamine6G | 558 | 195470 | 234000 | 0.8 |

A comparison of the ratio of fluorescence intensity before and after change in external environment (addition of 5 wt % SDS) among the fluorescent dye-encapsulating lactosomes is shown in Table 6 described below.

TABLE 6

| Dye | Fluorescence maximum (nm) | Fluorescence intensity (A) | Fluorescence intensity (PBS)(B) | Ratio of fluorescence intensity (A/B) |
|---|---|---|---|---|
| IC7-1 | 852 | 141929 | 694 | 204.5 |
| IC7-2 | 916 | 124942 | 15816 | 7.9 |
| ICG | 821 | 382900 | 5327 | 71.9 |
| IR820 | 849 | 97271 | 1103 | 88.2 |
| IR783 | 810 | 1037533 | 50920 | 20.4 |
| IR806 | 835 | 273806 | 29191 | 9.4 |
| Rhodamine 800 | 702 | 152580 | 80647 | 1.9 |
| Rhodamine 101 | 598 | 249130 | 162110 | 1.5 |
| Rhodamine6G | 560 | 242070 | 226800 | 1.1 |

In all the cases, the IC7-1-encapsulating lactosome had the highest ratio of fluorescence intensity in SDS, BSA, or plasma to that in PBS at the fluorescence maximum wavelength, followed by the IR820-encapsulating lactosome and the ICG-encapsulating lactosome (Tables 4 to 6). In the cases of the lactosomes encapsulating a fluorescent dye having a rhodamine skeleton, the fluorescence intensity ratio was 1.9 at most.

Example 6

Figure 6:
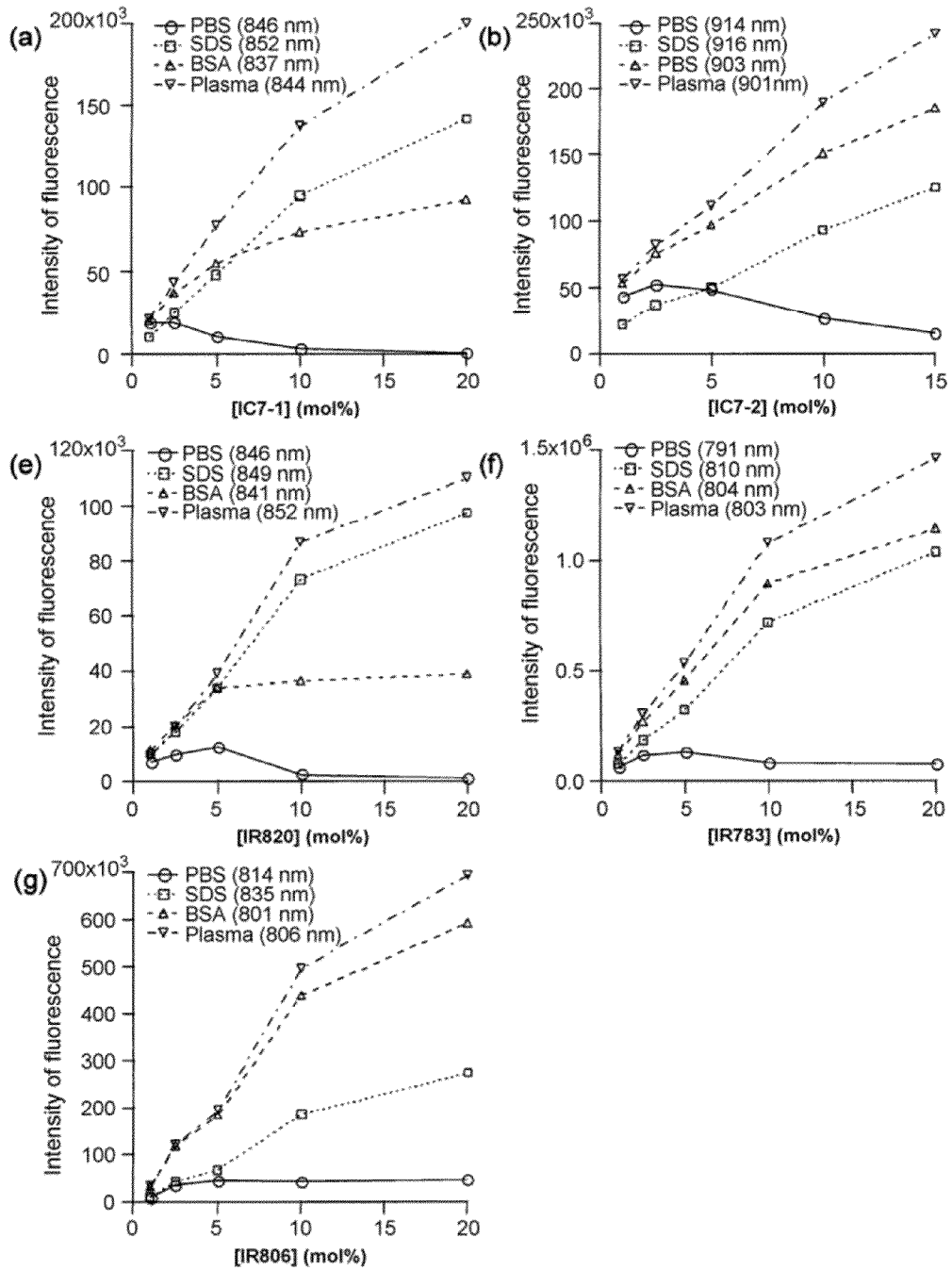
FIG. 6 shows the measurement results of fluorescence intensity when PBS, SOS, BSA, or plasma was added to fluorescent dye-encapsulating lactosomes (1 mg/mL) each prepared by changing the amount of a fluorescent dye (IC7-1 (a), IC7-2 (b), IR820 (e), IR783 (f), or IR806 (g)) encapsulated therein.

Dependence of Fluorescence Intensity of Fluorescent Dye-Encapsulating Lactosome on Fluorescent Dye Content Lactosomes encapsulating, as a fluorescent dye, IC7-1, IC7-2, IR820, IR783, or IR806 were prepared by changing the fluorescent dye content (1 mg/mL), and were then mixed with PBS, 5 wt % SDS, 5 wt % BSA, or plasma 1:1 (volume ratio), and the mixture was allowed to stand at room temperature for 30 minutes under lightproof conditions, and then diluted with PBS so that the concentration of the amphiphilic polymer was $1/15$ mg/mL to measure the intensity of fluorescence using Fluorolog-3 (HORIBA Jobin Yvon Inc.) (FIG. 6).

The fluorescent dye-encapsulating lactosomes had a tendency that the intensity of fluorescence in PBS was maximized when the IC7-1 content was 1 mol %, the IC7-2 content was 2.5 mol %, and the IR820, IR783, or IR806 content was 5 mol %, but was reduced when the IC7-1 content, the IC7-2 content, and the IR820, IR783, or IR806 content exceeded the above values, respectively.

When the fluorescent dye was IC7-1, IC7-2, IR783, or IR806, the intensity of fluorescence was increased with dependence on fluorescent dye content by adding SDS, BSA, or plasma. When the fluorescent dye was IR820, the intensity of fluorescence was increased with dependence on fluorescent dye content by adding SDS or plasma, but was almost constant even by adding BSA when the fluorescent dye content was 5 mol % or more.

Example 7

Figure 7:
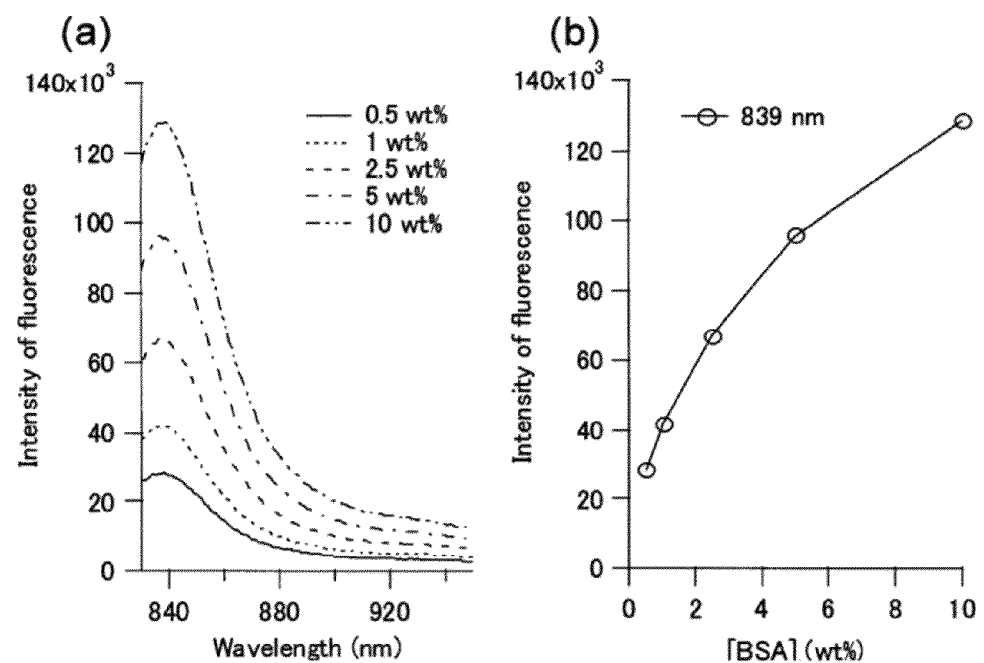
FIG. 7(a) shows the measurement results of fluorescence intensity when 0.5 to 10 wt % of BSA was mixed with lactosomes encapsulating 20 mol % of IC7-1.
FIG. 7(b) shows the relationship between the concentration of BSA and the fluorescence intensity at the fluorescence maximum value (839 nm).

Dependence of Fluorescence Intensity of Fluorescent Dye-Encapsulating Lactosome on BSA Concentration The results of fluorescence intensity measurement when 0.5 to 10 wt % of BSA was mixed with the lactosome encapsulating 20 mol % of IC7-1 are shown in FIG. 7(a), and the relationship between the concentration of BSA and the fluorescence intensity at fluorescence maximum (839 nm) is shown in FIG. 7(b). The fluorescence intensity of the IC7-1-encapsulating lactosome was increased with dependence on the concentration of BSA, and the fluorescence intensity when 10 wt % of BSA was added was about 4.5 times higher than that when 0.5 wt % of BSA was added. The molar ratio between encapsulated IC7-1 and BSA added is 1:2.3 to 1:47, and therefore, it is considered that the fluorescent dye encapsulated in the lactosome needs excessive BSA molecules to recover from a quenching state.

Example 8

Fluorescence Imaging Test of Subcutaneous Cancer Using IC7-1-Encapsulating Lactosomes Cancer-bearing mice were produced by subcutaneous transplantation of mouse cancer cells in the following manner.

As animals, 7-week-old Balb/c nu/nu mice (Clea) were used, and mouse ascites cancer cells (Ehrlich Ascites Tumor) were subcutaneously transplanted in the right thigh of each of the mice at $1 \times 10^6$ cells/0.05 mL. When the cancer tissue reached a size of 12 mm after growth for 2 weeks, each of the mice was subjected to the following imaging test.

Each of the cancer-bearing mice was anesthetized with isoflurane, and 0.05 mL of the dispersion liquid of lactosomes encapsulating 1 mol %, or 20 mol % of IC7-1 (0.13 nmol/body, or 3.2 nmol/body, respectively) was administered as molecular probes from its tail vein. After the administration of the probe dispersion liquid, fluorescence images of the whole body of each of the mice were taken with time. The fluorescence images of the whole body were taken from five directions, that is, from all the directions of left abdomen, left side of the body, back, right side of the body, and right abdomen of the mouse. The fluorescent dye was excited at 785 nm and fluorescence at about 845 nm was measured with time.

Figure 8:
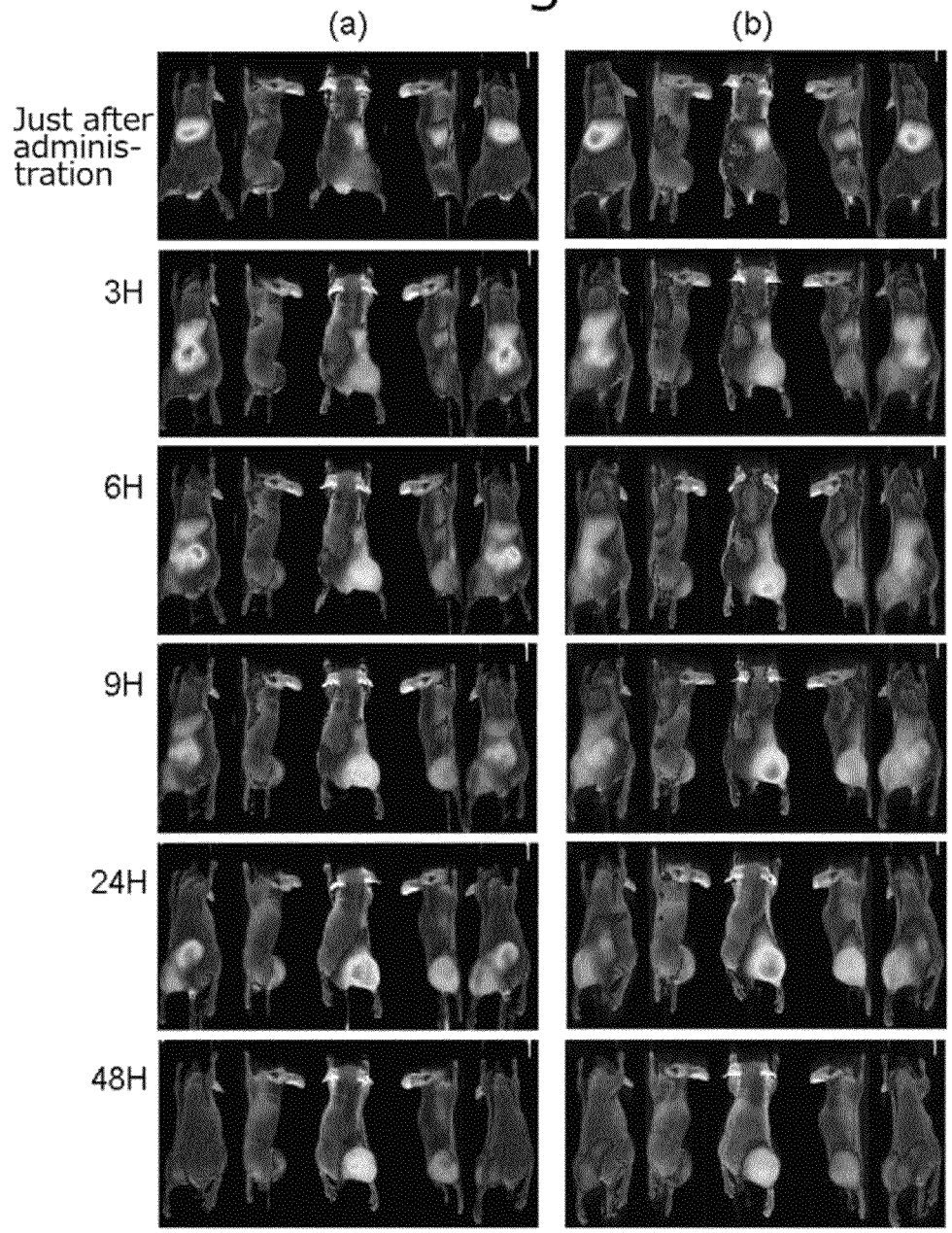
FIG. 8 shows the results of a fluorescence imaging test of a tumor-bearing mouse when lactosomes encapsulating 1 mol % of IC7-1 were used (a) and when lactosomes encapsulating 20 mol % of IC7-1 were used (b), wherein images were obtained by measuring the mouse from 5 directions (i.e., from the directions of its left abdomen, left side of the body, back, right side of the body, and right abdomen) just after tail vein injection of the fluorescent probe and after 3, 6, 9, 24, and 48 hours from the administration.

Images obtained when the 1 mol % IC7-1-encapsulating lactosome was used are shown in FIG. 8(a), and images obtained when the 20 mol % IC7-1-encapsulating lactosome was used are shown in FIG. 8(b). FIGS. 8(a) and 8(b) show the results of measurement performed just after tail vein injection of the nanoparticles into each of the mice and after 3 hours, 6 hours, 24 hours, and 48 hours from the administration. In FIG. 8, a difference in fluorescence intensity is indicated by a difference in color.

When the 1 mol % IC7-1-encapsulating lactosome was used, fluorescence was observed at the cancer site after 3 hours from the tail vein injection, and the intensity of fluorescence was gradually increased and maximized after 24 hours. Just after the administration, fluorescence was observed at the liver site. However, after 24 hours from the administration, fluorescence was hardly observed at the liver due to excretion of the fluorescent dye accumulated in the liver from the body. Also when the 20 mol % IC7-1-encapsulating lactosome was used, similar pharmacokinetics was observed.

Figure 9:
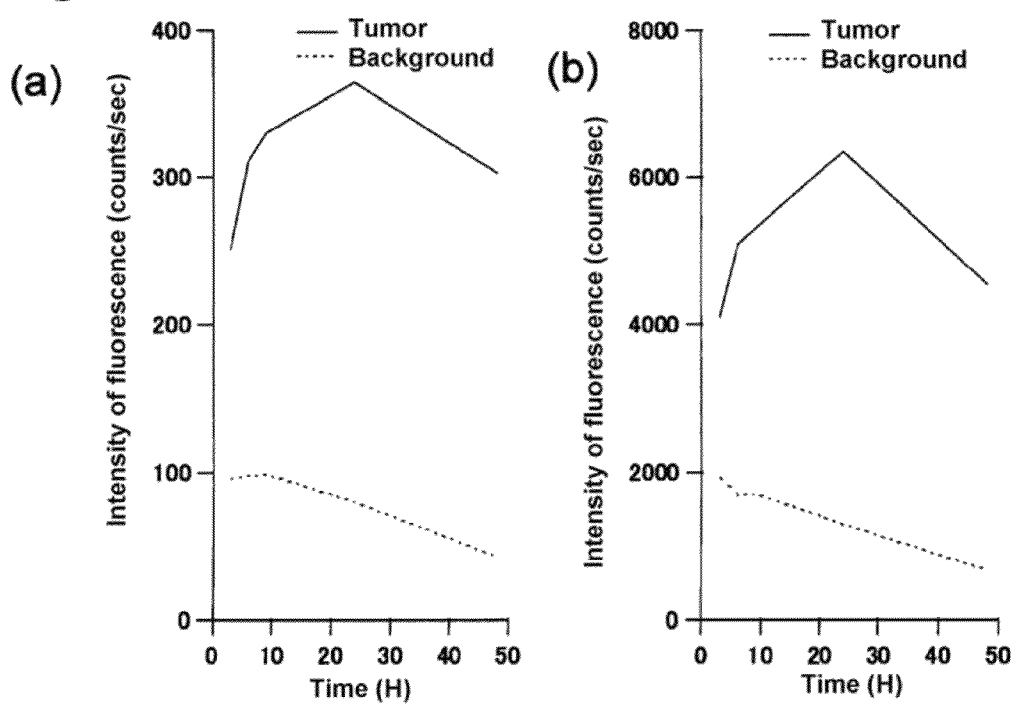
FIG. 9 shows the results of a comparison of fluorescence intensity in tumor measured from the direction of the back and fluorescence intensity in the back as a background between when lactosomes encapsulating 1 mol % of IC7-1 were used (a) and when lactosomes encapsulating 20 mol % of IC7-1 were used (b)

FIG. 9 shows the results of a comparison of fluorescence intensity in a cancer measured from a back direction and fluorescence intensity in the back as a background between when the 1 mol % IC7-1-encapsulating lactosome was used (a) and when the 20 mol % IC7-1-encapsulating lactosome was used (b). In FIG. 9, the horizontal axis represents elapsed time (Time (H)) after the tail vein injection of the nanoparticles, and the vertical axis represents the intensity of fluorescence (counts/sec) per second of exposure time.

When the 1 mol % or 20 mol % IC7-1-encapsulating lactosome was used, the average intensity of fluorescence after a lapse of 24 hours from the tail vein injection was about 350 or about 6,300, respectively. The intensity of fluorescence was about 18 times higher when the 20 mol % IC7-1-encapsulating lactosome was used in proportion to the amount of the fluorescent dye encapsulated in the lactosome.

This indicates that high-intensity fluorescence in a cancer can be observed by using lactosomes encapsulating a large amount of cyanine-based dye.

The invention claimed is:

1. A fluorescent nanoparticle probe comprising:
   a molecular assembly composed of an amphiphilie block polymer having a hydrophilic block chain and a hydrophobic block chain; and
   a fluorescent dye encapsulated in the molecular assembly, wherein
   the amphiphilic block polymer is selected from the group consisting of a polysarcosine-polylactic acid amphiphilic block polymer, a polyethylene glycol-polylactic acid amphiphilic block polymer, and a polysarcosine-poly(leucine-aminoisobutyric acid) amphiphilic block polymer, and
   the fluorescent dye is a cyanine compound represented by the following structural formula (I);

[Chemical formula 1]

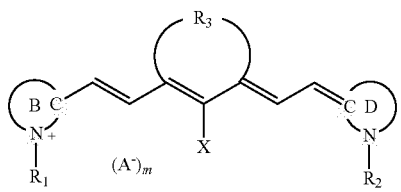

(I)

wherein R₁ and R₂ may be the same or different from each other and each is a hydrocarbon group Which may be substituted; R₃ is a bivalent hydrocarbon group which may be substituted;

X is a halogen, an aryloxy group, or a thioaryloxy group; A⁻ is an anion and m is 0 or 1; and a ring B and a ring D may be the same or different from each other and each is a nitrogen containing bicyclic or tricyclic aromatic heterocycle, and two or more molecules of the fluorescent dye are encapsulated in a self-quenching state by association in the single molecular assembly, wherein the fluorescent nanoparticle recovers fluorescence by contact with a blood component to deform the structure of the molecular assembly composed of an amphiphilic block polymer and to dissociate the association of the two or more molecules of the fluorescent dye; and wherein fluorescence intensity in plasma is 10 times or more higher than that in phosphate buffered saline.

2. The fluorescent nanoparticle probe according, to claim 1, wherein the fluorescent dye is encapsulated in the molecular assembly in an amount of 1to 50 mol % with respect to a total amount of the amphiphilic block polymer and the fluorescent dye.

3. The fluorescent nanoparticle probe according to claim 1, wherein the ring B has either of the following structures:

[Chemical formula 2]

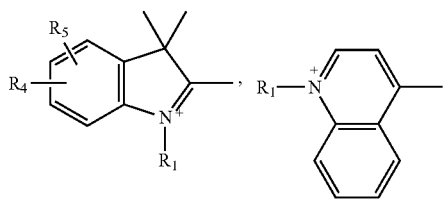

wherein R₄ and R₅ are hydrogen or are linked together to form an aryl ring; and
the ring D has either of the following structures:

[Chemical formula 3]

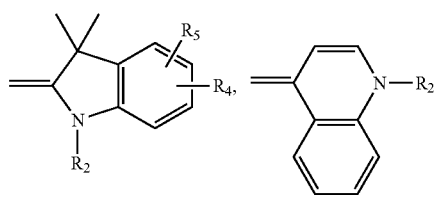

wherein R₄ and R₅ are hydrogen or are linked together to form an aryl ring.

4. The fluorescent nanoparticle probe according to claim 1, wherein the cyanine compound is an indocyanine compound represented by the following structural formula (I-i):

[Chemical formula 4]

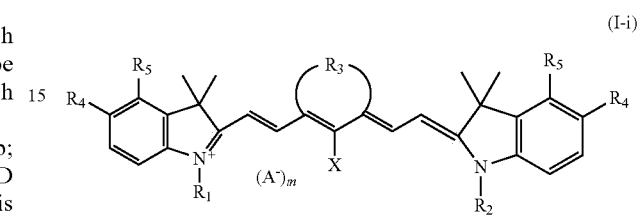

(I-i)

wherein R₄ and R₅ are hydrogen or are linked together to form an aryl ring.

5. The fluorescent nanoparticle probe according to claim 1, wherein the fluorescent dye is represented by the following structural formula (I-ii):

[Chemical formula 5]

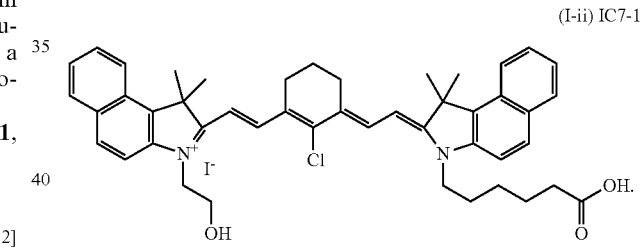

(I-ii) IC7-1

6. The fluorescent nanoparticle probe according to claim 1, wherein the fluorescent dye is represented by the following structural formula (I-iii):

[Chemical formula 6]

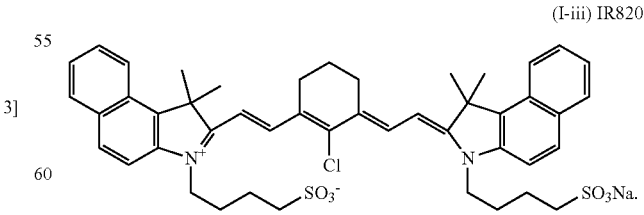

(I-iii) IR820

7. The fluorescent nanoparticie probe according to claim 1, wherein the fluorescent dye is represented by the following structural formula (I-iv):

[Chemical formula 7]

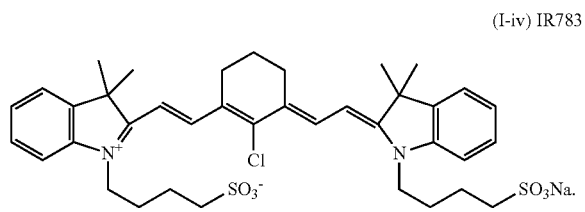
(I-iv) IR783

8. The fluorescent nanoparticle probe according to claim 1, wherein the fluorescent dye is represented by the following structural formula (I-v):

[Chemical formula 8]

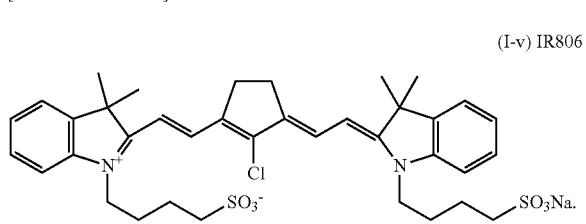
(I-v) IR806

9. The fluorescent nanoparticle probe according to claim 1, wherein the fluorescent dye is represented by the following structural formula (I-vi):

[Chemical formula 9]

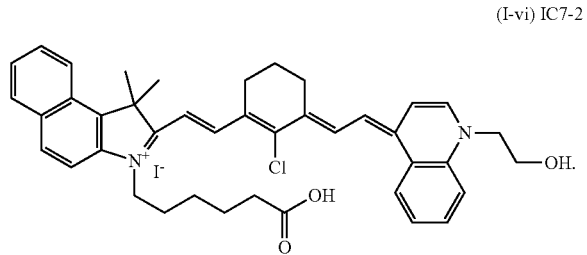
(I-vi) IC7-2

10. The fluorescent nanoparticle probe according to claim 1, wherein the fluorescent dye is represented by the following structural formula (I-vii):

[Chemical formula 10]

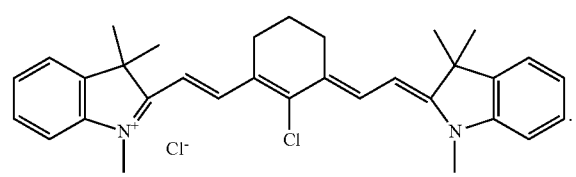
(I-vii) IR775

11. The fluorescent nanoparticle probe according to claim 1, wherein the fluorescent dye is represented by the following structural formula (I-viii):

[Chemical formula 11]

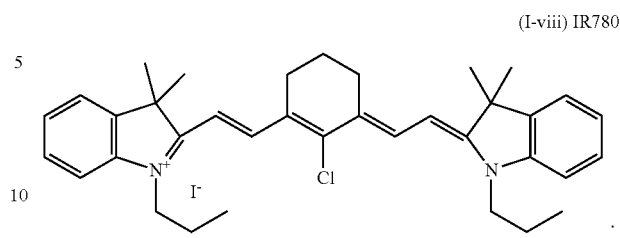
(I-viii) IR780

12. The fluorescent nanoparticle probe according to claim 1, wherein the fluorescent dye is represented by the following structural formula (I-ix):

[Chemical formula 12]

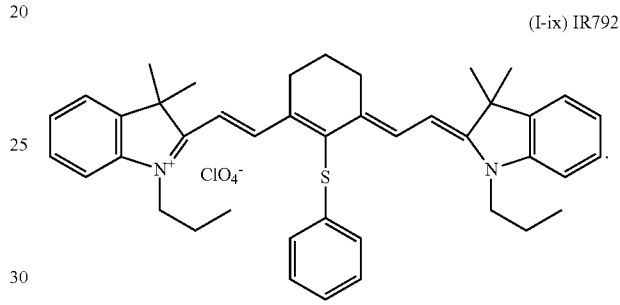
(I-ix) IR792

13. The fluorescent nanoparticle probe according to claim 1, wherein the fluorescent dye is represented by the following structural rafinula (I-x):

[Chemical formula 13]

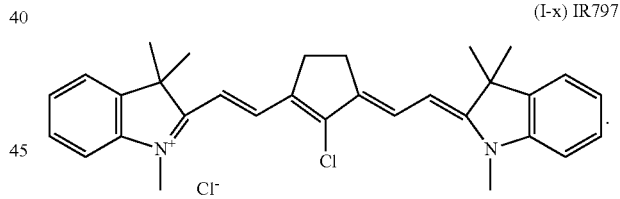
(I-x) IR797

14. The fluorescent nanoparticie probe according to claim 1, wherein the fluorescent dye is represented by the following structural formula (I-xi):

[Chemical formula 14]

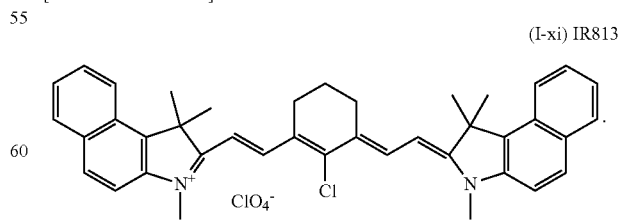
(I-xi) IR813

15. The fluorescent nanoparticle probe according to claim 1, wherein the hydrophobic block chain is a hydrophobic block chain having 25 or more lactic acid units.

16. A fluorescent molecular imaging method comprising the steps of: administering the fluorescent nanoparticle probe according to claim 1 to a non-human animal; and
detecting fluorescence.

* * * * *